(12) United States Patent
Fournial et al.

(10) Patent No.: US 9,050,477 B2
(45) Date of Patent: Jun. 9, 2015

(54) COSMETIC COMPOSITIONS COMPRISING ORIDONIN AND NEW COSMETIC USES

(75) Inventors: Arnaud Fournial, Paris (FR); Philippe Mondon, Paris (FR)

(73) Assignee: SEDERMA (FR)

( * ) Notice: Subject to any disclaimer, the term of this patent is extended or adjusted under 35 U.S.C. 154(b) by 109 days.

(21) Appl. No.: 13/264,547

(22) PCT Filed: Apr. 15, 2010

(86) PCT No.: PCT/IB2010/051651
§ 371 (c)(1),
(2), (4) Date: Oct. 14, 2011

(87) PCT Pub. No.: WO2010/119423
PCT Pub. Date: Oct. 21, 2010

(65) Prior Publication Data
US 2012/0028916 A1    Feb. 2, 2012

(30) Foreign Application Priority Data

Apr. 17, 2009   (FR) ..................... 09 01889

(51) Int. Cl.
| | | |
|---|---|---|
| A61K 31/704 | (2006.01) | |
| A61K 31/352 | (2006.01) | |
| A61P 17/18 | (2006.01) | |
| A61P 17/00 | (2006.01) | |
| A61Q 19/08 | (2006.01) | |
| A61K 8/34 | (2006.01) | |
| A61K 8/49 | (2006.01) | |
| A61Q 19/02 | (2006.01) | |

(52) U.S. Cl.
CPC ............... *A61Q 19/08* (2013.01); *A61K 8/347* (2013.01); *A61K 8/498* (2013.01); *A61Q 19/02* (2013.01)

(58) Field of Classification Search
CPC ....... A61K 8/347; A61K 8/498; A61Q 19/02; A61Q 19/08
USPC .................................................. 514/33, 453
See application file for complete search history.

(56) References Cited

U.S. PATENT DOCUMENTS

| | | |
|---|---|---|
| 1,985,424 A | 12/1934 | Piggott |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Schwartz |
| 2,703,798 A | 3/1955 | Schwartz |
| 2,798,053 A | 7/1957 | Brown |
| 2,809,971 A | 10/1957 | Bernstein |
| 2,826,551 A | 3/1958 | Geen |
| 2,965,576 A | 12/1960 | Wilson |
| 3,155,591 A | 11/1964 | Hilfer |
| 3,236,733 A | 2/1966 | Karsten et al. |
| 3,311,624 A | 3/1967 | Ohnacker et al. |
| 3,332,880 A | 7/1967 | Kesller et al. |
| 3,755,560 A | 8/1973 | Dickert |
| 3,761,418 A | 9/1973 | Parran, Jr. et al. |
| 3,929,678 A | 12/1975 | Laughlin et al. |
| 3,958,581 A | 5/1976 | Abegg et al. |
| 3,959,461 A | 5/1976 | Bailey et al. |
| 3,962,418 A | 6/1976 | Birkofer |
| 3,964,500 A | 6/1976 | Drakoff |
| 4,152,416 A | 5/1979 | Spitzer et al. |
| 4,202,879 A | 5/1980 | Shelton |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,387,090 A | 6/1983 | Bolich, Jr. |
| 4,421,769 A | 12/1983 | Dixon et al. |
| 4,470,982 A | 9/1984 | Winkler |
| 4,509,949 A | 4/1985 | Huang et al. |
| 4,557,853 A | 12/1985 | Collins |
| 4,599,379 A | 7/1986 | Flesher et al. |
| 4,628,078 A | 12/1986 | Glover et al. |
| 4,677,120 A | 6/1987 | Parish et al. |
| 4,741,855 A | 5/1988 | Grote et al. |
| 4,800,197 A | 1/1989 | Kowcz et al. |
| 4,816,261 A | 3/1989 | Luebbe et al. |
| 4,835,206 A | 5/1989 | Farrar et al. |
| 4,847,071 A | 7/1989 | Bissett et al. |
| 4,849,484 A | 7/1989 | Heard |
| 4,885,311 A | 12/1989 | Parish et al. |

(Continued)

FOREIGN PATENT DOCUMENTS

| | | |
|---|---|---|
| EP | 2 288 68 A2 | 7/1987 |
| EP | 330369 A1 | 8/1989 |

(Continued)

OTHER PUBLICATIONS

Ikezoe T. et al. (Mol Cancer Ther. Apr. 2005;4(4):578-86).*
Herouy et al.; Eur. J. Dermatology, Apr.-May 2000, 10:3, pp. 173-180.
Woessner, J.F.; Faseb J., 1991, vol. 5, pp. 2145-2154.
Wang, S.; A Chinese Medicinal Tincture for the Treatment of Arthragia Syndrome and Pyocutaneous Disease, 2008, Chemical Abstracts Service, XP002625388.
International Search Report for PCT/IB2010/051651 dated Mar. 14, 2011.

(Continued)

*Primary Examiner* — Janet Epps-Smith
*Assistant Examiner* — Courtney Brown
(74) *Attorney, Agent, or Firm* — Lerner, David, Littenberg, Krumholz & Mentlik, LLP

(57) ABSTRACT

The present invention related to cosmetic compositions comprising oridonin and new cosmetic uses. Oridonin is used for fighting the signs of cutaneous aging and for slimming. A composition comprising a combination of oridonin and darutigenol or a derivative thereof, in particular darutoside, is disclosed together with the cosmetic use of such composition.

28 Claims, 2 Drawing Sheets

(56) References Cited

U.S. PATENT DOCUMENTS

| | | |
|---|---|---|
| 4,960,764 A | 10/1990 | Figueroa, Jr. et al. |
| 4,970,252 A | 11/1990 | Sakuta et al. |
| 4,976,953 A | 12/1990 | Orr et al. |
| 5,011,681 A | 4/1991 | Ciotti et al. |
| 5,049,584 A | 9/1991 | Purcell et al. |
| 5,073,371 A | 12/1991 | Turner et al. |
| 5,073,372 A | 12/1991 | Turner et al. |
| 5,087,445 A | 2/1992 | Haffey et al. |
| 5,100,660 A | 3/1992 | Hawe et al. |
| 5,104,646 A | 4/1992 | Bolich, Jr. et al. |
| 5,106,609 A | 4/1992 | Bolich, Jr. et al. |
| 5,120,532 A | 6/1992 | Wells et al. |
| 5,124,356 A | 6/1992 | Purcell et al. |
| RE34,075 E | 9/1992 | Purcell et al. |
| 5,151,209 A | 9/1992 | McCall et al. |
| 5,151,210 A | 9/1992 | Steuri et al. |
| RE34,584 E | 4/1994 | Grote et al. |
| 5,412,004 A | 5/1995 | Tachibana et al. |
| 5,487,884 A | 1/1996 | Bissett et al. |
| 5,607,980 A | 3/1997 | McAtee et al. |
| 5,652,228 A | 7/1997 | Bissett |
| 5,654,362 A | 8/1997 | Schulz, Jr. et al. |
| 5,681,852 A | 10/1997 | Bissett |
| 5,686,082 A | 11/1997 | N'Guyen |
| 5,736,537 A | 4/1998 | Gubernick et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,939,082 A | 8/1999 | Oblong et al. |
| 6,068,834 A | 5/2000 | Kvalnes et al. |
| 6,159,485 A | 12/2000 | Yu et al. |
| 6,190,645 B1 | 2/2001 | SaNogueira et al. |
| 6,372,717 B1 | 4/2002 | Greff |
| 6,620,419 B1 | 9/2003 | Lintner |
| 2005/0048008 A1* | 3/2005 | Gupta .......................... 424/59 |

FOREIGN PATENT DOCUMENTS

| | | |
|---|---|---|
| EP | 0518772 A1 | 12/1992 |
| EP | 0518773 A1 | 12/1992 |
| EP | 2026780 A1 | 11/2007 |
| FR | 00/03846 M | 12/1964 |
| FR | 2654619 A1 | 5/1991 |
| FR | 2694195 A1 | 2/1994 |
| FR | 2702766 A1 | 9/1994 |
| FR | 2723314 A1 | 2/1996 |
| FR | 2 732 215 A1 | 10/1996 |
| FR | 2733149 A1 | 10/1996 |
| FR | 2771002 A1 | 5/1999 |
| FR | 2781231 A1 | 1/2000 |
| FR | 2788058 A1 | 7/2000 |
| FR | 2831444 A1 | 5/2003 |
| FR | 2854897 A1 | 11/2004 |
| FR | 2855057 A1 | 11/2004 |
| GB | 849 433 A | 9/1960 |
| GB | 2 274 585 A | 8/1994 |
| JP | 63-141915 A | 6/1988 |
| JP | 5105613 A | 4/1993 |
| JP | 7069886 A | 3/1995 |
| JP | 5105613 A * | 4/2003 |
| WO | 91/16034 A1 | 10/1991 |
| WO | 91/16035 A1 | 10/1991 |
| WO | 93/23028 A1 | 11/1993 |
| WO | 95/34280 A1 | 12/1995 |
| WO | 96/33689 A1 | 10/1996 |
| WO | 97/05856 A1 | 2/1997 |
| WO | 98/05299 A1 | 2/1998 |
| WO | 98/07744 A1 | 2/1998 |
| WO | 98/43607 A1 | 10/1998 |
| WO | 99/18927 A1 | 4/1999 |
| WO | 99/25369 A1 | 5/1999 |
| WO | 9940897 A1 | 8/1999 |
| WO | 00/15188 A1 | 3/2000 |
| WO | 00/40611 A1 | 7/2000 |
| WO | 00/43417 A1 | 7/2000 |
| WO | 00/58347 A1 | 10/2000 |
| WO | 01/43701 A2 | 6/2001 |
| WO | 01/64178 A1 | 9/2001 |
| WO | 02/15871 A1 | 2/2002 |
| WO | 02/66668 A2 | 8/2002 |
| WO | 02/076423 A2 | 10/2002 |
| WO | 03/024418 A2 | 3/2003 |
| WO | 03017966 A2 | 3/2003 |
| WO | 03/028692 A2 | 4/2003 |
| WO | 03/068141 A2 | 8/2003 |
| WO | 2004/024695 A1 | 3/2004 |
| WO | 2004062637 A1 | 7/2004 |
| WO | 2004/101609 A2 | 11/2004 |
| WO | 2007/132190 A1 | 11/2007 |

\* cited by examiner

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 1

Lys Thr Thr Lys Ser
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Arg Ser Arg Lys
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 3

Gly Gln Pro Arg
1

<210> SEQ ID NO 4
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The N terminal can be amidated by a Palmitoyl
      chain

<400> SEQUENCE: 4

Val Gly Val Ala Pro Gly
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
```

-continued

```
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa is either Met or Leu

<400> SEQUENCE: 5

Tyr Gly Gly Phe Xaa
1               5
```

COSMETIC COMPOSITIONS COMPRISING ORIDONIN AND NEW COSMETIC USES

CROSS-REFERENCE TO RELATED APPLICATIONS

The present application is a national phase entry under 35 U.S.C. §371 of International Application No. PCT/IB2010/051651 filed Apr. 15, 2010, published in English, which claims priority from FR0901889 filed Apr. 17, 2009, all of which are incorporated herein by reference.

TECHNICAL FIELD

The present invention concerns the cosmetic use of oridonin to fight the cutaneous signs of aging. It also concerns a cosmetic composition comprising oridonin and darutigenol or a derivative thereof like darutoside and its use in cosmetic fields.

The present invention relates to the industries of chemical, cosmetical or care products for skin and its appendages (like hair, eyelashes, eyebrows, nails, hairs) of mammalians, animals or humans.

BACKGROUND ART

During aging, a progressive decline in the functions of the skin is observed and gives rise, among other things, to the emergence of heterogeneity of the skin. Thus, with aging, the skin changes, this gradually affects its appearance: redness, blemishes, wrinkles, firmness, or smooth.

Skin aging does not result from a single phenomenon but is multifactorial. Three components may be cited: a genetic component, an environmental component and a behavioral component. Alone or in combination, the three components induce, at a variable rate, profound changes in the structure and quality of the skin that are frequently visible on the surface of the skin.

Thus, the cosmetic industries are constantly looking for new compounds able to offer beauty and vitality prolonged skin.

Therefore, the technical problem to resolve was for the inventors of the present invention to find compounds able to act remarkably against the damaging effects of aging skin.

Oridonin is a known molecule corresponding to the following formula:

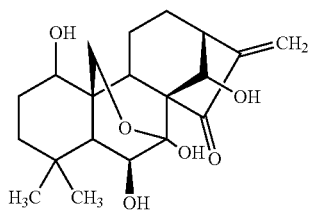 [SMILES: C=C1C(=O)[C@@]23C(O)[C@@H]1CCC2[C@]12COC3(O)[C@@H](O)C1C(C)(C)CCC2O]

Oridonin has been tested in vitro, in particular as an active principle for the treatment of human cancer resistant to Taxol (EP2026780). Oridonin is also disclosed in document JP63141915 as a compound able to stimulate hair growth.

SUMMARY OF THE INVENTION

However, nothing in the prior art suggests the use of oridonin to remedy to esthetical cutaneous disorders linked to aging. Thus, the solution of the technical problem is the cosmetic use of oridonin to fight the signs of cutaneous aging. Thanks to the use of oridonin, excellent results have been shown by the inventors of the present invention.

The appearance of the skin tissue is greatly improved: the wrinkles and fine lines are blurred, the visible and/or tactile discontinuities are diminished; skin is firmer, more toned and thus more elastic.

The skin is better protected against free radicals. Free radicals are considered one of the causes of skin aging, especially as regards the appearance of wrinkles. In particular, free radicals cause direct damage to biological molecules of importance: DNA, proteins, lipids, but also secondary lesions by creating toxic byproducts. Oxygen thus generates different reactive forms including hydrogen peroxide which produces the very reactive hydroxyl radical. To control these oxidising species, the cell uses antioxidant strategies. Among endogen compounds, reduced glutathione can be found, a tripeptide which is the major actor of antioxidising defense, fighting against oxygen radicals but also against peroxides and NO. The inventors of the present invention have thus found that oridonin stimulated the synthesis of reduced glutathion and thus was an excellent detoxifying agent: the skin is detoxified, less dull, it breathes.

The distribution and repartition of the chromophores of the skin is more homogeneous thanks to the use of oridonin. The apparent rednesses are reduced; complexion is more uniform, smooth and bright.

Chromophores are colored molecules. In the skin, the teen refers to molecules able to absorb light and whose accumulation is readily perceived by the eyes.

One the most known cutaneous chromophores is a red chromophore: the haemoglobin.

The distribution of this chromophore in young skins is very homogeneous, ie with no apparent blood vessels and no localized rednesses. With age and repeated daily minor stresses, the situation tends to change. The skin loses its homogeneity due to the impairment of chromophore balance (DEMIRLI et al, 2007). The vascularization becomes more visible at particular places, frequently those most exposed to the sun, either in the form of vessels or in the form of diffuse red areas of variable intensity (YAAR, 2006).

In addition to this chromophore, visible to the naked eye, dermal collagen also has the ability to absorb certain types of photon and thus constitutes a particular chromophore.

Collagen can now be measured using systems that "see" through the skin. It is known that, with age and stress, collagen, which is a protein of the extracellular matrix, is less produced and exhibit greater degradation. This weakens the supporting network of the skin, once again heterogeneously. This degradation renders the skin thinner and underlying structures and defects become visible.

The cutaneous heterogeneity of these two chromophores can be monitored using recently developed systems such as the SIAscope® and VISTA® (Montcrieff et al, 2002; Demilri et al, 2007; Matts et al, 2007).

Thus, a first object of the invention related to the cosmetic use of oridonin to fight the signs of skin aging. According to the invention, "fight the signs of skin aging" means a treatment against:
- wrinkles, fine lines, visible and/or tactile skin discontinuities, loss of firmness, elasticity and tone of skin tissue;
- oxidative stress and free radicals;
- altered distribution of chromophores, thus rebalancing the distributed haemoglobin and collagen in the skin and thereby reduce in particular skin rednesses.

To this aim, the inventors of the present invention propose to combine oridonin with at least one of the following compound: fatty acids (oils comprising DHA/EPA, shea butter, PUFAs, LIPEXEL™), moisturizing agents (HYDRAPROTECTOL™, MOIST-24™), humectants (glycerin, glycols and polyols), plant extracts like blueberry extract, PHYTOTAL™, PHYTEXCELL™, *Boswellia Serrata* Gum (boswellic acid), Pilewort extract (*Ranunculus Ficaria*), saponins, *Skeletonema costatum* extract, birch sap extract (*Betula Alba*) (Sève de Bouleau™/Birch Sap™ of SEDERMA, WO 03/024418), *Bacopa Monnieri* extract (Bacocalmine™ of SEDERMA, WO 99/40897), rose extracts, bisabolol, D-panthenol, madecassoside, *centella asiatica* extract, potassium glycyrrhizinate or cafein, seaweed extracts, amino acids, peptides (MATRIXYL®, MATRIXYL® 3000, DERMAXYL™, RIGIN™, copper peptides, Biopeptide CL™, Biopeptide EL™, SYNAKE®, ARGIRELINE®), enzymes (VENUCEANE™, KERATOLINE™), coenzymes (ubiquinone Q10, coenzyme A, R) and co-factors (NADH, NAD, SAM), lightening agents (MAP, LUMISKIN™, MELASLOW™), allantoine, farnesol, polyphenols (HELIOGENOL™), anti-inflammatory agents (bisabolol, NDGA, bacosides, esculosides, Kawain), oligo- and polysaccharides, flavonoids, phytosterols, di- and triterpens, tannins, alpha- et beta-hydroxy acids, fermentation products (BIODERMINE™, OXYLASTIL™, PHOSPHOVITAL™), Dynalift™, Essenskin™, teprenone (Renovage™, Sederma) and derivatives and structural analogues, Tyr-Arg dipeptide and derivatives comprising N-Acetyl-Tyrosyl-Arginyl-Hexadecyl ester (Calmosensine™, Sederma), *Arnica Montana* Flower/*Cupressus Sempervirens* Seed/*Polygonatum Multiflorum* extracts (Phytotonine™, Sederma), noraporphines such as glaucine, boldine, diacetylboldine.

More particularly, oridonin is combined with at least one compound stimulating the extracellular matrix selected from:

Vitamin A and in particular retinoid retinoic acid, retinol, retinoic acid, retinyl proprionate retinol palmitate, Vitamin B3 and more particularly niacinamide, tocopherol nicotinate, Vitamin B5, vitamin B6, vitamin B12, Vitamin C, in particular ascorbic acid, ascorbyl acid, glucoside ascorbyl, tetrapalmitate ascorbyl, magnesium and sodium ascorbyl phosphate, Vitamins E, F, H, K, PP, Metalloproteinase inhibitor, TIMP activator, DHEA, precursors and derivatives, Amino acids, such arginine, ornithine, hydroxyproline, hydroxyproline dipalmitate, Palmitoylglycine, hydroxylysine, methionine and derivatives, Peptides such commercially known under the names: MATRIXYL®, MATRIXYL® 3000, DERMAXYL™, RIGIN™, copper peptides, Biopeptide CL™, Carnosine, Biopeptide EL™, SYNAKE™, ARGIRELINE™, Allantoin, farnesol, CAPILECTINE™, ANCRINE™, PROCAPYL™, CAPIGEN™, CAPISLOW™, biotine, Minoxidil®, Adenosine, Lactic acid, glycolic acid, glucosamine, acetylglucosamine, madecassic acid, asiaticoside and asiatic acids, ellagic acid, salicylic acid, stigmasterol, sitosterol, campesterol and brassicasterol, teprenone, Genistein, equol, hexamidine, panthenol, dimethylaminoethanol (DMAE), Oils comprising DHA/EPA, shea butter, glycerin, Darutigenol and derivatives, and more particularly darutoside.

Preferably, oridinin is combined with darutigenol or combined with darutoside.

Darutigenol has the following formula:

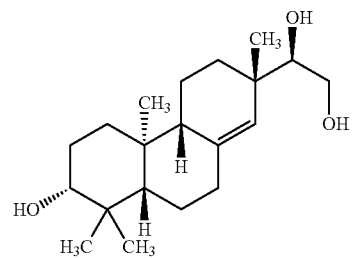

while darutoside corresponds to a sugar derivative form of darutigenol, having the following formula:

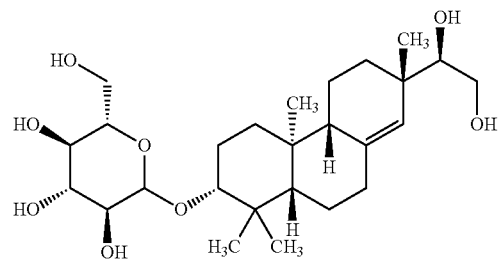

Thus, according to a second object, the invention relates to a composition comprising, in a physiologically acceptable medium, an effective amount of oridonin and darutigenol or a derivative of darutigenol, more particularly darutoside, as active agents.

More particularly, the invention relates to a composition comprising, in a physiologically acceptable medium, an effective amount of oridonin and darutoside.

Within the scope of the present invention, oridonin, darutigenol and darutoside can be obtained from any supply source, especially by means of hemi chemical synthesis, chemical synthesis, enzymatic, by one of the many methodologies of biotechnology, by plant extraction or by any other means used to obtain it at reasonable cost in the end-product to be used industrially.

According to an embodiment, the extraction is vegetal and oridonin is extracted from *Rabdosia rubescens*, meanwhile darutigenol and darutoside are extracted from *Siegesbeckia orientalis*. *Siegesbeckia orientalis*, a plant also known as "holy herb" or "St. Paul's wort". Native to India, the plant has spread to various tropical countries including Madagascar, where it is used by the locals as a medicinal plant with a soothing and cicatrizing effect (BOITEAU, 1993).

The plant extraction can be made by the usual techniques, for example by phenolic extraction, using any part of the plant as the flower, seed, fruit, root, tuber, leaf, pericarp. The extraction solvents can be selected from water, propylen glycol, butylen glycol, glycerin, PEG-6 Caprylic/capric glycerides, polyethylene glycol, methylic and/or ethylic ethers of diglycols, cyclic polyols, ethoxylated or propoxylated diglycols, alcohols (methanol, ethanol, propanol, butanol), or a mixture of these solvents. Furthermore, it is possible to produce extracts of the present invention by other methods such as, for example, maceration, simple decoction, leaching, extraction under reflux, supercritical $CO_2$ extraction, the extraction with ultrasound or microwaves or finally using counter-current techniques, this list being not limited.

The molecule of darutoside can be found under the trade name Darutigenol™.

The mixtures oridonin/darutigenol or oridonin/darutoside according to the invention provides, through a synergistic effect, an enhanced cosmetic activity as shown by the in vitro and in vivo results that are given thereafter.

Thus, the present invention also relates to the cosmetic use of a composition comprising oridonin and darutigenol, or the use of a composition comprising oridonin and darutoside, said composition being intended to fight the signs of skin aging, including for example:

- wrinkles, fine lines, visible and/or tactile discontinuities of the skin, loss of firmness, elasticity and tone of the skin tissues induced inter alia by oxidative stress and free radicals;
- the alteration of the distribution of chromophores, thus rebalancing the distribution of haemoglobin and collagen in the skin.

Oridonin combined to darutigenol or darutoside also helps reduce age or melanin spots and reduce or eliminate the cutaneous rednesses.

According to the present invention, oridonin or a combination of oridonin and darutigenol or a combination of oridonin and darutoside, is combined with a suitable excipient, that is to say a physiologically acceptable medium. "Physiological medium" means according to the present invention, without limitation, an aqueous or alcoholic, a water-in-oil, an oil-in-water microemulsion, an aqueous gel, an anhydrous gel, a serum, a dispersion of vesicles.

"Physiologically acceptable" means that the compositions or compounds described are suitable for use in contact with mucous membranes, nails, scalp, hair, hairs and skin of mammals and particularly human without risk of toxicity, of incompatibility, instability, allergic response, and others.

The amount of oridonin in a composition is ranging from 0.00001% to 50%, preferably 0.0001% to 10%, more preferably 0.001% to 3% by weight to the total weight of the composition.

The amount of darutigenol or derivative thereof (in particular darutoside) is ranging from 0.00001% to 80%, preferably 0.001% to 50%, more preferably 0.01% to 3% by weight to the total weight of the composition.

Preferably, the weight ratio of oridonin/darutigenol or derivative thereof (in particular darutoside) is ranging from 1:1000 to 10:1, preferably 1:1000 and 1:1, more preferably 1:100 and 1:1.

It is particularly interesting to associate oridonin with sunscreens or organic or inorganic UV filters. The organic UV filters particularly preferred are chosen from the following compounds: Ethylhexyl Salicylate, Butyl methoxydibenzoylmethane, Ethylhexyl Methoxycinnamate, Octocrylene, phenylbenzimidazole sulfonic acid, Terephthalylidene Dicamphor sulfonic acid, benzophenone-3, Benzophenone-4, Benzophenone-5,4 methylbenzylidene camphor, Benzimidazilate, Anisotriazine, Ethylhexyl triazone, diethylhexyl Butamido triazone, Methylene bis-Benzotriazolyl Tetramethylbutylphenol, Drometrizole trisiloxane, and mixtures thereof. The inorganic UV filters particularly preferred are nanopigments of titanium oxide (amorphous or crystallized in rutile and/or anatase forms), iron, zinc, zirconium or cerium. Coating agents are moreover alumina and/or aluminum stearate. A preferred $TiO_2/MnO_2$ sunscreen is Optisol™ proposed by Oxonica.

The terms "adjuvant", "additives" and "optional compound" are used as a synonym for "additional ingredients". "The active substances" are synonyms of "active ingredients".

All percentages and ratios used in this application are by weight of total composition and all measurements are made at 25° C. unless it is specified otherwise.

In addition, the inventors have also found slimming effects, including reducing the expansion and/or preventing the installation of adipose tissue through the cosmetic use of oridonin.

Thus, according to another aspect of the invention, it has been discovered that the oridonin possesses remarkable properties as a slimming agent.

The inventors recommend to combine oridonin with different compounds known for their slimming action such as *Centella asiatica*, asiaticoside and asiatic acid, caffein, thein and methyl xanthines, theophylline, theobromine, forskolin, esculin and esculoside, ACE inhibitors, Val-Trp, Captopryl™, inhibitors of Neuropeptide Y, enkephalin, *gingko biloba*, yam, *Dioscorea* extracts, rutin extract, yerba mate extract, guarana extract, oligosaccharides, exopolysaccharides, alcohol, carnitine, ivy extract, fucus extract, algae extract, extract of *Peumus Boldus*, palmitoylcamitine, carnosine, taurine, cyclic AMP, elderberry extract, Phtyosonic™, Vexel™, Coaxel™, Pleurimincyl™, Lipocare™, Unislim™, Bodyfit™, noraporphines and their derivatives.

Furthermore, oridonin can be combined with one or more other active ingredients in order advantageously to obtain a cosmetic product having an even wider range of properties. Thus, the composition of the present invention may contain at least one additional active agent chosen in particular among anti-aging, whitening, moisturizing, slimming, anti-acne, anti-inflammatory and anti-hair loss agents, as described below in the detailed description of the invention.

According to an embodiment, it is proposed to combine the composition of oridonin and darutigenol or the composition of oridonin and darutoside with the ingredient(s) sold by Sederma VENUCEANE™ (an anti ageing agent containing thermus thermophilus ferment) and/or OLIGOCEANE (a revitalizer agent containing mineral salts, trace elements in particular, extracted from marine sediments and oyster shells).

DETAILED DESCRIPTION

Figure 1:
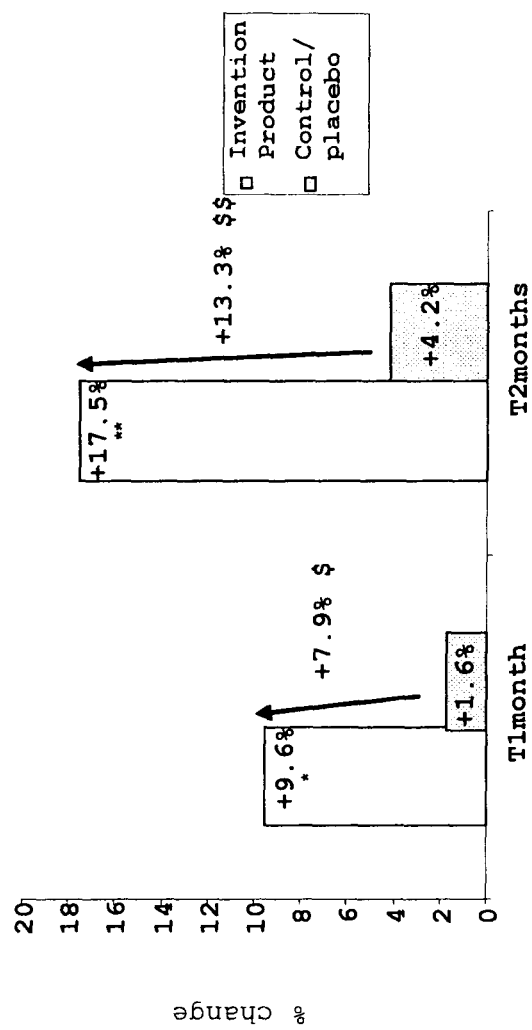
FIG. 1 depicts change in dermal collagen density of the neckline determined using echography (Echography+image analysis, n=25). Data indicate that with the cream according to the invention, there was a marked increase in the most echogenic zones reflecting an increase in the density of dermal fibers such as collagen. The increase, which was noteworthy and significant as of the first month of application, increased further after 2 months, reaching 17.5% (p<0.01). In parallel, the control site showed little change. * p<0.05 versus TO/** p<0.01 versus TO/$ p<0.05 versus control/$$ p<0.01 versus control.
Figure 2:
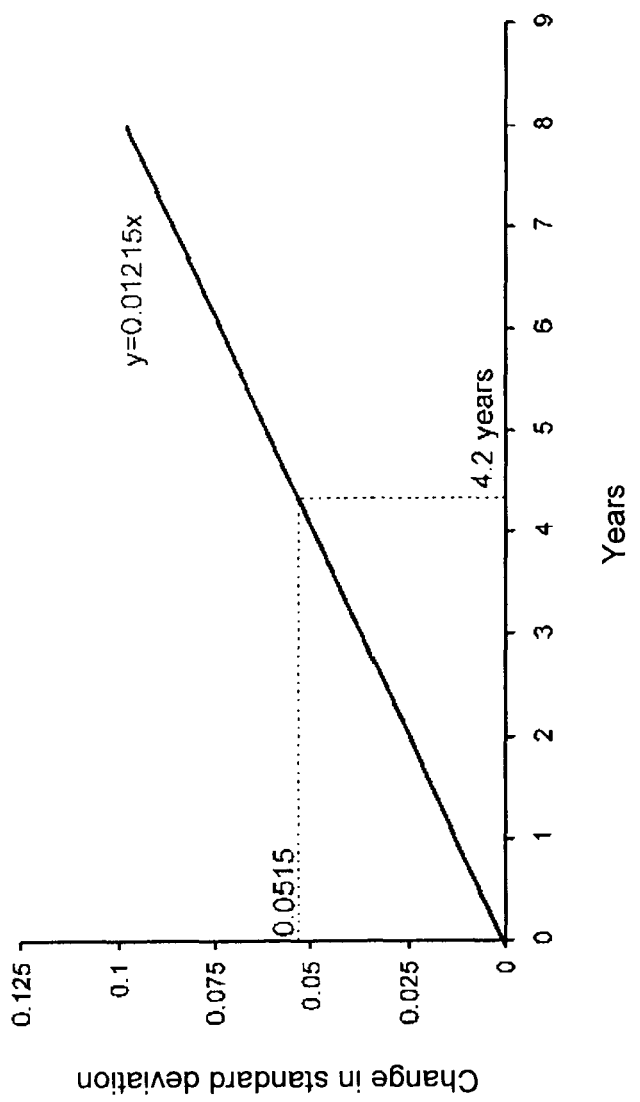
FIG. 2 depicts collagen heterogeneity, and the correlation between the change in standard deviation and change in theoretical age with regard to the data presented in Table 15. The results obtained were correlated with published results (MATTS et al., 2005) in order to express the pre- vs. post-change in the heterogeneity of collagen distribution (equivalent to a standard deviation) as a variation in age.

The present invention will be better understood from the following description.

The term "cosmetic composition" or simply "composition" according to the present invention, concerns a formulation which may be used for cosmetic or hygiene purposes or as a base for one or more pharmaceutical ingredients. These also include cosmetics, personal care products and pharmaceutical preparations. It is also possible that these formulations may be used for two or more purposes at the same time. A medical anti-dandruff shampoo, for example, has pharmacological properties and is used as a personal care product to obtain healthy hair.

Some compositions from the present invention may also provide additional benefits including stability, lack of significant irritation of the skin (unacceptable to the consumer), anti-inflammatory activity and good aesthetics.

I. ADDITIVES

The compositions of the invention may include various additional other ingredients, conventional or not. Of course, a decision to include an additional ingredient and the choice of a specific active ingredient and of additional ingredients depends on the specific application and product formulation. The line of demarcation between an "active" ingredient and an "additional" ingredient is therefore artificial and depends on the specific application and product type. A substance that is an "active" ingredient in one application or product may be a "functional" ingredient in another, and vice versa.

The compositions of the invention may include one or more additional ingredients, various, conventional or not, which will provide some benefit to the object of the composition. Such additional ingredients may include one or more substances such as, without limitations, cleaning agents, hair conditioning agents, skin conditioning agents, hair styling agents, antidandruff agents, hair growth promoters, perfumes, sunscreen and/or sunblock compounds, pigments, moisturizers, film formers, hair colors, make-up agents, detergents, pharmaceuticals, thickening agents, emulsifiers, humectants, emollients, antiseptic agents, deodorant actives, surfactants and propellants.

In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment.

The CTFA Cosmetic Ingredient Handbook, Tenth Edition (published by the Cosmetic, Toiletry, and Fragrance Association, Inc., Washington D.C.) (2004) describes a non limited wide variety of cosmetic and pharmaceutical ingredients usually used in the skin care industry that can be used as additional ingredients in the compositions of the present invention. Examples of these ingredient classes include, but are not limited to: healing agents, skin anti-aging agents, skin moisturizing agents, anti-wrinkle agents, anti-atrophy agents, skin smoothing agents, antibacterial agents, antifungal agents, pesticides anti parasitic agents, antimicrobial agents, anti-inflammatory agents, anti-pruriginous agents, external anesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, depigmenting or propigmenting agents, antiglycation agents, tightening agents, agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, plant extracts, plant derivatives, plant tissue extracts, plant seed extracts, plant oils, botanicals, botanical extracts, ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, and vitamins and derivatives thereof, peeling agents, moisturizing agents, curative agents, lignans, preservatives, UV absorbers, a cytotoxic, an antineoplastic agent, a fat-soluble active, suspending agents, viscosity modifiers, dyes, nonvolatile solvents, diluents, pearlescent aids, foam boosters, a vaccine, and their mixture.

Said additional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, lys-thr-thr-lys-ser (SEQ ID NO: 1), palmitoyl-lys-thr-thr-lys-ser (SEQ ID NO:1), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoïdes, ceramides and pseudo-ceramides, a lipid complex, oils in general of natural origin such shea butter, apricot oil, onagre oil, prunus oil, palm oil, monoi oil, HEPES; procysteine; O-octanoyl-6-D-maltose; the disodium salt of methylglycinediacetic acid, steroids such as diosgenin and derivatives of DHEA; DHEA or dehydroepiandrosterone and/or a precursor or chemical or biological derivative, N-ethyloxycarbonyl-4-para-aminophenol, bilberry extracts; phytohormones; extracts of the yeast *Saccharomyces cerevisiae*; extracts of algae; extracts of soyabean, lupin, maize and/or pea; alverine and its salts, in particular alverine citrate, extract of butcher's broom and of horse chestnut, and mixtures thereof, a metalloproteinase inhibitor.

Further skin care and hair care active ingredients that are particularly useful in combination with the tri/tetrapeptide mixture can be found in SEDERMA commercial literature and on the website www.sederma.fr. (herewith incorporated in its entirety).

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

1) Sugar Amines (Amino Sugars)

The compositions of the present invention can comprise a sugar amine, which is also known as amino sugar. Sugar amine compounds useful in the present invention can include those described in PCT Publication WO 02/076423 and U.S. Pat. No. 6,159,485.

In one embodiment, the composition comprises from about 0.01% to about 15%, more preferably from about 0.1% to about 10%, and even more preferably from about 0.5% to about 5% by weight of the composition, of sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

2) DHEA

The composition of the present invention may comprise DHEA or dehydroepiandrosterone and/or a precursor or biological or chemical derivative.

The term "DHEA precursor" concerns biological precursors of said DHEA which are likely to transform in DHEA during metabolism, as well as its chemical precursors which are likely to transform in DHEA by exogen chemical reaction. As non limiting examples of biological precursors, A5-pregnenolone, 17ahydroxy pregnenolone and 17ahydroxy pregnenolone sulfate can be cited. Also, as non limitating examples of chemical precursors, the sapogenins or their derivatives, such as diosgenine (or spriost-5-en-3-beta-ol), hecogenin, hecogenin acetate, smilagenine and sarsasapogenine, as well as the natural extracts containing them, in particular fenugrec and Disocorees extracts such as the wild igname roots or Wild Yam, can be cited.

The term "DHEA derivatives" comprises its chemical derivatives as well as its biological derivatives. As biological derivatives, A5-androstene-3,7-diol and A4-androstene-3,17-dione can be cited. DHEA salts, in particular hydrosoluble salts, like DHEA sulfate, can be cited as non limiting examples of chemical derivatives. Esters, such hydroxcarboxylic acid or DHEA esters disclosed for example in U.S. Pat. No. 5,736,537, or other esters such DHEA salicilate, acetate, valerate (or nheptanoate) and enanthate can also be cited. Derivatives of DHEA (DHEA carbamates, DHEA 2-hydroxy malonate, DHEA aminoacid esters) disclosed in FR 00/03846 in the name of the Applicant can be cited. This list is obviously not exhaustive.

3) Metalloproteinase Inhibitors

The term "metalloproteinase inhibitor" relates to all molecule and/or plant or bacterial extract having a inhibitory activity on at least one of the metalloproteinases expressed or synthetized by or in the skin. The article of Y. HEROUY and al., European Journal of Dermatology, n 3, vol. 10, Avril-Mai 2000 discloses metalloproteinases (pp. 173-180). The family of the metalloproteinases is formed of several well-defined groups on the basis of their resemblance regarding structure and substrat specificity (Woessner J. F., Faseb Journal, vol. 5, 1991, 2145). Among these groups, there are collagenases able to degrade fibrillar collagens (MMP-1 or interstitial collagenase, MMP-8 or neutrophil collagenase, MMP-13 or collagenase 3, MMP-18 or collagenase 4), gelatinases degrading type IV collagen or other denatured collagen form (MMP-2 or A gelatinase (72 kDa), MMP-9 or B gelatinase (92 kDa)), stromelysines (MMP-3 or stromelysine 1, MMP-10 or stromelysine 2, MMP-11 or stromelysine 3) whose broad spectrum of activity targets proteins of the extracellular matrix such as glycoproteins (fibronectine, laminine), proteoglycannes etc., matrilysine (MMP-7), metalloelastase (MMP-12) or also ou encore les membrane metalloproteinases (MMP-14, MMP-15, MMP-16 et MMP-17). Metalloproteinases (MMPs) are proteases that use a metal, mostly zinc coordinated to 3 cystein residues and to a methionine in their active site and that degrade macromolecular components of the extracellulare matrix and of basal layers at neutral pH (collagen, elastin, etc. . . . ). This group of enzymes is inactivated by metal chelators.

The principal activity regulators of MMPs are the tissue inhibitors of metalloproteinases or TIMPs such TIMP-1, TIMP-2, TIMP-3 and TIMP-4 (Woessner J. F., Faseb Journal, 1991). Furthermore, the MMPs expression is also regulated by growth factors, cytokins, oncogens products (ras, jun), or also matrice constituants.

The term "metalloproteinase inhibitors>> according to the present invention means all molecule able to reduce the MMPs activity regarding the gene expression (transcription and translation) or regarding the activation of the zymogene form of MMPs, or else regarding the local control of active forms.

Furthermore, the metalloproteinase inhibitors according to the present invention can also be MMP-1 inhibitors of natural or synthetic origin. The terms "natural origin" or "synthetic origin" mean both a metalloproteinase inhibitor at a pure state or in solution at different concentrations, but natural inhibitors are obtained from different extraction methods of a natural origin term element (for example the lycopene) whereas the inhibitors of synthetical origin are all obtained via chemical synthesis.

4) Vitamin B3 Compounds

The compositions of the present invention can include a vitamin B3 compound. Vitamin B3 compounds are particularly useful for regulating skin conditions, as described in U.S. Pat. No. 5,939,082. In one embodiment, the composition comprises from about 0.001% to about 50%, more preferably from about 0.01% to about 20%, even more preferably from about 0.05% to about 10%, and still more preferably from about 0.1% to about 7%, even more preferably from about 0.5% to about 5%, by weight of the composition, of the vitamin B3 compound.

As used herein, "vitamin B3 compound" means a compound having the formula:

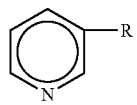

wherein R is —CONH2 (i.e., niacinamide), —COOH (i.e., nicotinic acid) or —CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g, tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of C1-C22, preferably C1-C16, more preferably C1-C6 alcohols. Non-vasodilating esters of nicotinic acid include tocopherol nicotinate and inositol hexanicotinate; tocopherol nicotinate is preferred.

Other derivatives of the vitamin B3 compound are derivatives of niacinamide resulting from substitution of one or more of the amide group hydrogens. Specific examples of such derivatives include nicotinuric acid (C8H8N2O3) and nicotinyl hydroxamic acid (C6H6N2O2).

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, and niaprazine.

Examples of the above vitamin B3 compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin B3 compounds may be used herein. Preferred vitamin B3 compounds are niacinamide and tocopherol nicotinate. Niacinamide is more preferred.

When used, salts, derivatives, and salt derivatives of niacinamide are preferably those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate, preferably chloride), and organic carboxylic acid salts (including mono-, di- and tri-C1-C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan ("The Reaction of L-Ascorbic and D-Iosascorbic Acid with Nicotinic Acid and Its Amide", J. Organic Chemistry, Vol. 14, 22-26 (1949)).

The vitamin B3 compound may be included as the substantially pure material, or as an extract obtained by suitable physical and/or chemical isolation from natural (e.g., plant) sources. The vitamin B3 compound is preferably substantially pure, more preferably essentially pure.

5) Dehydro Acetic Acid (DHA)

The composition of this invention can include dehydroacetic acid, having the structure:

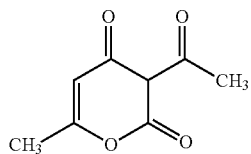

or pharmaceutically acceptable salts, derivatives or tautomers thereof. The technical name for dehydroacetic acid is 3-Acetyl-6-methyl-2H-pyran-2,4(3H)-dione and can be commercially purchased from Lonza.

Pharmaceutically acceptable salts include alkali metal salts, such as sodium and potassium; alkaline earth metal salts, such as calcium and magnesium; non-toxic heavy metal salts; ammonium salts; and trialkylammonium salts, such astrimethylammonium and triethylammonium. Sodium, potassium, and ammonium salts of dehydroacetic acid are preferred. Highly preferred is sodium dehydroacetate which can be purchased from Tri-K, as Tristat SDHA. Derivatives of dehydroacetic acid include, but are not limited to, any compounds wherein the CH3 groups are individually or in combination replaced by amides, esters, amino groups, alkyls, and alcohol esters. Tautomers of dehydroacetic acid can be described as having the chemical formula C8H8O4 and generally having the structure above.

In one embodiment, the compositions of the present invention can comprise from about 0.001% to about 25% by weight of the composition, preferably from about 0.01% to about 10%, more preferably from about 0.05% to about 5%, and even more preferably from about 0.1% to about 1%, of dehydroacetic acid or pharmaceutically acceptable salts, derivatives or tautomers thereof.

6) Phytosterol

The compositions of the present invention can comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. More preferably, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company, and Cognis.

In one embodiment, the composition of the present invention comprises from about 0.0001% to about 25%, more preferably from about 0.001% to about 15%, even more preferably from about 0.01% to about 10%, still more preferably from about 0.1% to about 5%, and even more preferably from about 0.2% to about 2% phytosterol, by weight of the composition.

7) Salicylic Acid Compound

The compositions of the present invention may comprise a salicylic acid compound, its esters, its salts, or combinations thereof. In one embodiment of the compositions of the present invention, the salicylic acid compound preferably comprises from about 0.0001% to about 25%, more preferably from about 0.001% to about 15%, even more preferably from about 0.01% to about 10%, still more preferably from about 0.1% to about 5%, and even more preferably from about 0.2% to about 2%, by weight of the composition, of salicylic acid.

8) Hexamidine

The compositions of the present invention can include hexamidine compounds, its salts, and derivatives. In one embodiment, the hexamidine comprises from about 0.0001% to about 25%, more preferably from about 0.001% to about 10%, more preferably from about 0.01% to about 5%, and even more preferably from about 0.02% to about 2.5% by weight of the composition.

As used herein, hexamidine derivatives include any isomers and tautomers of hexamidine compounds including but not limited to organic acids and mineral acids, for example sulfonic acid, carboxylic acid, etc. Preferably, the hexamidine compounds include hexamidine diisethionate, commercially available as Eleastab® HP100 from Laboratoires Serobiologiques.

9) Dialkanoyl Hydroxyproline Compounds

The compositions of the present invention can comprise one or more dialkanoyl hydroxyproline compounds and their salts and derivatives.

In one embodiment, the dialkanoyl hydroxyproline compounds preferably comprise from about 0.01% to about 10%, more preferably from about 0.1% to about 5%, even more preferably from about 0.1% to about 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline.

10) Flavonoids.

The compositions of the present invention can comprise a flavonoid compound. Flavonoids are broadly disclosed in U.S. Pat. Nos. 5,686,082 and 5,686,367. As used herein, "flavonoid" means unsubstituted flavonoïd or substituted flavonoid (i.e. mono-substituted flavonoid, or/and di-substituted flavonoid, or/and tri-substituted flavonoid). Examples of flavonoids particularly suitable for use in the present invention are one or more flavones, one or more flavanones, one or more isoflavones, one or more coumarins, one or more chromones, one or more dicoumarols, one or more chromanones, one or more chromanols, isomers (e.g., cis/trans isomers) thereof, and mixtures thereof.

Preferred for use herein are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Also preferred are favanones such as hesperitin, hesperidin, and mixtures thereof.

Flavonoid compounds useful herein are commercially available from a number of sources, e.g., Indofine Chemical Company, Inc., Steraloids, Inc., and Aldrich Chemical Company, Inc. Suitable flavonoïdes are commercially available called Sterocare® offered by SEDERMA and described in WO 99/18927.

In one embodiment, the herein described flavonoid compounds comprise from about 0.01% to about 20%, more preferably from about 0.1% to about 10%, and even more preferably from about 0.5% to about 5%, by weight of the composition.

11) N-Acyl Amino Acid Compound

The topical compositions of the present invention can comprise one or more N-acyl amino acid compounds. The amino acid can be one of any of the amino acids known in the art. The N-acyl amino acid compounds of the present invention can correspond to the formula:

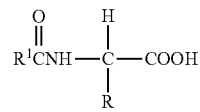

wherein R can be a hydrogen, alkyl (substituted or unsubstituted, branched or straight chain), or a combination of alkyl and aromatic groups.

Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof Among the broad class of N-acyl Phenylalanine derivatives, particularly useful is N-undecylenoyl-L-phenylalanine commercially available under the tradename Sepiwhite® from SEPPIC.

In one embodiment, of the present invention, the N-acyl amino acid preferably comprises from about 0.0001% to about 25%, more preferably from about 0.001% to about 10%, more preferably from about 0.01% to about 5%, and even more preferably from about 0.02% to about 2.5% by weight of the composition.

12) Retinoid

The compositions of this invention can comprise a retinoid, preferably in a safe and effective amount such that the resultant composition is safe and effective for regulating keratinous tissue condition, preferably for regulating visible and/or tactile discontinuities in keratinous tissue (e.g., regulating signs of skin aging). The compositions can comprise from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company, and Boerhinger Mannheim. Other retinoids which are useful herein are described in U.S. Pat. No. 4,677,120, U.S. Pat. No. 4,885,311, U.S. Pat. No. 5,049,584, U.S. Pat. No. 5,124,356, and Reissue 34,075. Other suitable retinoids can include tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids include retinol, retinyl palmitate, retinyl acetate, retinyl propionate, retinal and combinations thereof. More preferred is retinyl propionate, used most preferably from about 0.1% to about 0.3%.

The retinoid may be included as the substantially pure material, or as an extract obtained by suitable physical and/or chemical isolation from natural (e.g., plant) sources. The retinoid is preferably substantially pure, more preferably essentially pure.

13) Optional Peptide

The composition of the present invention can comprise an additional peptide. Suitable peptides can include, but are not limited to, di-, tri-, tetra-, penta-, and hexa-peptides and derivatives thereof. In one embodiment, the composition comprises from about 1×10-7% to about 20%, more preferably from about 1×10-6% to about 10%, even more preferably from about 1×10-5% to about 5%, by weight of additional peptide.

As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Suitable dipeptides for use herein include but are not limited to Carnosine (beta-Ala-His), Tyr-Arg, Val-Trp (WO 0164178), Asn-Phe, Asp-Phe. Suitable tripeptides for use herein include, but are not limited to Arg-Lys-Arg (Peptide CK), His-Gly-Gly. Gly-His-Lys, Gly-Gly-His, Gly-His-Gy, Lys-Phe-Lys. Suitable tetrapeptides for use herein include but are not limited to, Peptide E, Arg-Ser-Arg-Lys (SEQ ID NO: 2), Gly-Gln-Pro-Arg (SEQ ID NO: 3). Suitable pentapeptides include, but are not limited to Lys-Thr-Thr-Lys-Ser (SEQ ID NO: 1). Suitable hexapeptides include but are not limited to Val-Gly-Val-Ala-Pro-Gly (SEQ ID NO: 4) and such as those disclosed in FR 2854897 and US 2004/0120918.

Other suitable peptides for use herein include, but are not limited to lipophilic derivatives of peptides, preferably palmitoyl derivatives, and metal complexes of the aforementioned (e.g., copper complex of the tripeptide His-Gly-Gly). Preferred dipeptide derivatives include N-Palmitoyl-beta-Ala-His, N-Acetyl-Tyr-Arg-hexadecylester (CALMOSENSINE™ from SEDERMA, France, WO 9807744, U.S. Pat. No. 6,372,717). Preferred tripeptide derivatives include N-Palmitoyl-Gly-Lys-His, (Pal-GKH from SEDERMA, France, WO 0040611), a copper derivative of His-Gly-Gly sold commercially as lamin, from Sigma, lipospondin (N-Elaidoyl-Lys-Phe-Lys) and its analogs of conservative substitution, N-Acetyl-Arg-Lys-Arg-NH2 (Peptide CK+), N-Biot-Gly-His-Lys (N-Biot-GHK from SEDERMA, WO0058347) and derivatives thereof. Suitable tetrapeptide derivatives for use herein include, but are not limited to N-palmitoyl-Gly-Gln-Pro-Arg (SEQ ID NO: 3) (from SEDERMA, France), suitable pentapeptide derivatives for use herein include, but are not limited to N-Palmitoyl-Lys-Thr-Thr-Lys-Ser (SEQ ID NO: 1) (available as MATRIXYL™ from SEDERMA, France, WO 0015188 and U.S. Pat. No. 6,620,419) N-Palmitoyl-Tyr-Gly-Gly-Phe-X with X Met or Leu or mixtures thereof (SEQ ID NO: 5). Suitable hexapeptide derivatives for use herein include, but are not limited to N-Palmitoyl-Val-Gly-Val-Ala-Pro-Gly (SEQ ED NO: 4) and derivatives thereof.

The preferred compositions commercially available containing a tripeptide or a derivative include Biopeptide-CL™ by SEDERMA (WO0143701), Maxilip™ by SEDERMA (WO 0143701), Biobustyl™ by SEDERMA. The compositions commercially available preferred sources of tetrapeptides include RIGIN™ (WO0043417), EYELISS™ (WO03068141), MATRIXYL™ RELOADED, and MATRIXYL 3000™ which contain between 50 and 500 ppm of palmitoyl-Gly-Gln-Pro-Arg (SEQ ID NO: 3), and carrier, proposed by SEDERMA, France (US2004/0132667).

14) Ascorbates and Other Vitamins

The compositions of the present invention may comprise one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate). Such vitamins can include, but are not limited to, vitamin B, vitamin B derivatives, vitamin B1 to vitamin B12 and theirs derivatives, vitamin K, vitamin K derivatives, vitamin H vitamin D, vitamin D derivatives, vitamin E, vitamin E derivatives, and provitamins thereof, such as panthenol and mixtures thereof. The vitamin compounds may be included as the substantially pure material, or as an extract obtained by suitable physical and/or chemical isolation from natural (e.g., plant) sources. In one embodiment, when vitamin compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the vitamin compound.

15) Particulate Material

The compositions of the present invention can comprise one or more particulate materials. Non limiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, spherical particles of polyamide and more specifically Nylon 12, especially such as those sold by Atochem under the name Orgasol 2002D Nat C05, polystyrene microspheres such as for example those sold by Dyno Particles under the name Dynospheres, ethylene acrylate copolymer sold by Kobo under the name FloBead EA209, PTFE, polypropylene, aluminum starch ocetenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof.

Also useful herein are interference pigments. The most common examples of interference pigments are micas layered with about 50-300 nm films of TiO2, Fe2O3, silica, tin oxide, and/or Cr2O3. Useful interference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls) and Eckart (e.g. Prestige Silk Red).

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred.

16) Sunscreen Actives

The compositions of the subject invention may optionally contain a sunscreen active. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic screening agents which are active in UV-A and/or UV-B, there may be mentioned in particular those designated below by their CTFA name:

para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONA/EM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, ββ'-diphenylacrylate derivatives: Octocrylene sold in particular under the trademark "UVINUL N539" by BASF, Etocrylene, sold in particular under the trademark "UVINUL N35" by BASF, benzophenone derivatives: Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof.

others: dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl) ether; hydroquinone;

The organic UV-screening agents which are more particularly preferred are chosen from the following compounds: Ethylhexyl Salicylate, Butyl Methoxydibenzoylmethane, Ethylhexyl Methoxycinnamate, Octocrylene, Phenylbenzimidazole Sulphonic Acid, Terephthalylidene Dicamphor Sulphonic, Benzophenone-3, Benzophenone-4, Benzophenone-5,4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof.

Also preferred are the compositions described in U.S. Pat. No. 6,190,645 and in particular, sunscreen agents sold under the trademark INCROQUAT-UV-283 manufactured by Croda, Inc.

The inorganic screening agents which may be used in the composition according to the invention are in particular nanopigments (mean size of the primary particles: generally between 5 nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate. Such nanopigments of metal oxides, coated or uncoated, are in particular described in EP-A-0-518,772 and EP-A-0-518,773.

When used herein, the inorganic sunscreens are present in the amount of from about 0.1% to about 20%, preferably from about 0.5% to about 10%, more preferably from about 1% to about 5%, by weight of the composition.

17) Anti-Cellulite Agents

The compositions of the present invention may also comprise an anti-cellulite agent. Suitable agents may include, but are not limited to, xanthine compounds (e.g., caffeine, theophylline, theobromine, and aminophylline In one embodiment, when anti-cellulite compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-cellulite compound.

Especially useful are combinations with the cellulite/slimming agents called Vexel™ (FR 2 654 619), Coaxel (FR 2 694 195), Cyclolipase™ (FR 2 733 149), Pleurimincyl™ and Lipocare™ (WO 98/43607) and Unislim™ (FR 0306063), all offered by SEDERMA.

18) Slimming, Toning or Draining Actives

The compositions can include one or more lipolytic agent selected among: phosphodiesterase inhibitors (e.g., xanthine derivatives), alpha-2 blockers compounds capable of blocking alpha-2 receptors at the adipocytes surface, beta-adrenergical agonists and antagonists (e.g. alverine and its organic or inorganic salts such as alverine citrate), agents inhibiting LDL and VLDL receptors synthesis, inhibitors of enzymes of fatty acid synthesis such as acetylCoA carboxylase, or fatty acid synthetase or cerulenine, compounds stimulating beta receptors and/or G proteins, glucose transport blockers such as serutine or rutine, neuropeptide Y (NPY) antagonists capable of blocking NPY receptors at the adipocytes surface, cAMP and its cosmetically acceptable derivatives, adenylate cyclase enzyme active agents such as forskolin, agents modifying fat acids transport, lipolytic peptides and lipolytic proteins, like peptides or proteins such as the peptides derived from the parathyroidal hormone, described in particular in the patents FR 2788058 and FR 2781231.

Others examples of usable lipolytic agents include botanical and marine extracts.

among plant extracts, there may more particularly be mentioned the extract of English ivy (*Hedera Helix*), of Chinese thorowax (*Bupleurum chinensis*), of arnica (*Arnica Montana* L), of rosemary (*Rosmarinus officinalis* N), of marigold (*Calendula officinalis*), of sage (*Salvia officinalis* L), of ginseng (*Panax ginseng*), of *ginko biloba*, of St.-John's-Wort (*Hypericum Perforatum*), of butcher's-broom (*Ruscus aculeatus* L), of European meadowsweet (*Filipendula ulmaria* L), of big-flowered Jarva tea (*Orthosiphon Stamincus Benth*), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, extracts of escine, extracts of cangzhu, extracts of chrysanthellum indicum, extracts of the plants of the *Armeniacea* genus, Atractylodis Platicodon, Sinnomenum, Pharbitidis, Flemingia, extracts of *Coleus* such as *C. Forskohlii, C. blumei, C. esquirolii, C. scutellaroides, C. xanthantus* and *C. Barbatus*, such as the extract of root of *Coleus barbatus*, extracts of Ballote, extracts of Guioa, of Davallia, of Terminalia, of Barringtonia, of Trema, of antirobia, cecropia, argania, dioscoreae such as *Dioscorea opposita* or Mexican, as extracted of marine origin: extracts of algae or phytoplankton such as an extract of Laminaria digitata, diatoms, rhodysterol. All these extracts can of course to be taken in mixtures.

The compositions according to the invention can also contain in addition one or more additional active selected among: agents acting on the microcirculation (vasculoprotectors or vasodilators) such as the natural flavonoides, ruscogenines, esculosides, escine, nicotinates, heperidine methyl chalcone, butcher's-broom, essential oils of lavender or rosemary, the extracts of Ammi visnaga; anti-glycation agents such as extracts of *Centella asiatica* and *Siegesbeckia*, silicium, amadorine, ergothioneine and its derivatives, hydroxystilbenes and their derivatives (e.g. resvératrol), vegetable extracts of the family of Ericaceae, in particular bilberry extracts (*Vaccinium angustifollium*), vitamin C and its derivatives, retionol and its derivatives.

19) Butylated Hydroxytoluene (BHT) and Butylated Hydroxyanisole (BHA)

The topical compositions of the present invention may comprise BHT or BHA.

In one embodiment, BHT and/or BHA comprises from about 0.0001% to about 20% by weight of the composition, more preferably from about 0.001% to about 10%, even more preferably from about 0.01% to about 5%, and still more preferably from about 0.1% to about 0.5%.

20) Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

21) Desquamation Actives/Keratolytic Actives

A desquamating/keratolytic active may be added to the compositions of the present invention. In one embodiment, the composition comprises from about 0.01% to about 10%, preferably from about 0.1% to about 5%, more preferably from about 0.5% to about 2%, by weight of the composition, of a desquamating/keratolytic active.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2hydroxynonanoic acid; 2-hydroxydecanoic acid; 2-hydroxyundecanoic acid; 2-hydroxydodecanoic acid (alpha-hydroxylauric acid); 2-hydroxytetradecanoic acid (alpha-hydroxymyristic acid); 2-hydroxyhexadecanoic acid (alpha-hydroxypalmitic acid); 2-hydroxyoctadecanoic acid (alpha-hydroxystearic acid); 2-hydroxyeicosanoic acid (alpha-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyl lactic acid); 2-phenyl 2-methyl 2-hydroxyethanoic acid (atrolactic acid); 2-(4'-hydroxyphenyl) 2-hydroxyethanoic acid; 2-(4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3'-(2-hydroxyphenyl) 2-hydroxypropanoic acid; 3-(4'-hydroxyphenyl) 2-hydroxypropanoic acid; and 2-(3',4'dihydroxyphenyl), and 2-hydroxyethanoic acid, 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Preferred keratolytic agents are selected from the group comprising glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcine, retinoic acid, adapalene, trichloroacetic acid, 5-fluoro uracil, azelaic acid. Keratolytic agents are also the salts, esters, possible cis or trans forms, racemic mixtures and/or the relative dextrorotatory or levorotatory forms of the above listed compounds. Such substances can be used singularly or in associations with each other.

Other keratolytic agents suitable for use herein can include enzymatic exfoliant based on a protease called Keratoline™ and offered by Sederma.

One desquamation system that is suitable for use herein comprises salicylic acid and zwitterionic surfactants and is described in U.S. Pat. No. 5,652,228. Another desquamation system that is suitable for use herein contains sulfhydryl compounds and zwitterionic surfactants and is described in U.S. Pat. No. 5,681,852. Zwitterionic surfactants such as those described in this referenced patent can also be useful as desquamatory agents herein, with cetyl betaine being particularly preferred.

22) Anti-Acne Actives

The compositions of the present invention can comprise one or more anti-acne actives. Examples of useful anti-acne actives include resorcinol, sulfur, erythromycin, salicylic acid, benzoyl peroxide, dehydroacetic acid and zinc. Further examples of suitable anti-acne actives are described in U.S. Pat. No. 5,607,980. Especially useful are combinations with the anti-acne ingredient called Ac.net™ offered by SEDERMA (WO 03/028692 A2).

In one embodiment, when anti-acne compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-acne compound.

23) Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol, hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid (vitamin), stilbenes, cinnamates, resveratrol, kinetin, zeatin, dimethylaminoethanol, peptides from natural sources (e.g., soy peptides), and salts of sugar acids (e.g., Mn gluconate, Zn gluconate), lipoic acid; lysophosphatidic acid, skin peel agents (e.g., phenol and the like), vitamin B3 compounds and retinoids and other vitamin B compounds (e.g., thiamine (vitamin B1), pantothenic acid (vitamin B5), riboflavin (vitamin B2), and their derivatives and salts (e.g., HCL salts or calcium salts). Especially useful are combinations with the wrinkle agents called Dermolectine™ and Sterocare™ offered by SEDERMA (WO99/18927).

In one embodiment, when anti-wrinkle/anti-atrophy compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-wrinkle/anti-atrophy compound.

24) Anti-Oxidants/Radical Scavengers

The compositions of the present invention can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lycine pidolate, arginine pilolate, amino acids, silymarin, lysine, 1-methionine, proline, superoxide dismutase, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, melanin, rosemary extracts and grape skin/seed extracts may be used. Preferred anti-oxidants/radical scavengers can be selected from esters of tocopherol, more preferably tocopherol acetate and tocopherol sorbate (U.S. Pat. No. 4,847,071)

25) Humectants, Moisturizers and Conditioning Agents

The compositions of the present invention can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953.

Also useful are various C1-C30 monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

Humectants can be selected from the group consisting of polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

26) Active Oxygen Generation Inhibitors

The compositions of the present invention may also comprise a an active oxygen generation inhibitor selected from the group comprising quercetin, rutin, taxifolin, kaempferol, myricetin, curcumin, resveratrol, arecoline, apigenin, wogonin, luteolin, tectorigenin, and a mixture thereof.

This active oxygen generation inhibitor may be contained in an amount of about 0.001% to about 5%, more preferably in an amount of about 0.01% to about 3%%, by weight of the composition.

27) Chelators

The compositions of the present invention may also comprise a chelator or chelating agent. As used herein, "chelator" or "chelating agent" means an active agent capable of removing a metal ion from a system by forming a complex so that the metal ion cannot readily participate in or catalyze oxygen radical formation. In one embodiment, a chelating agent is added to a composition of the present invention, preferably from about 0.00001% to about 10%, more preferably from about 0.001% to about 5%, by weight of the composition. Exemplary chelators that are useful herein include those that are disclosed in U.S. Pat. No. 5,487,884, WO 91/16035 and WO 91/16034. Examples of chelating agents include N-hydroxysuccinimide, EDTA, NTA, deferoxamine, hydroxamic acids and their salts, phytic acid, phytate, gluconic acid and its salts, transferrine, lactoferrin; furildioxime and derivatives thereof.

28) Anti-Inflammatory Agents

An anti-inflammatory agent may be added to the compositions of the present invention. In one embodiment, an anti-inflammatory agent is added at a level of from about 0.01% to about 10%, preferably from about 0.5% to about 5%, by weight of the composition. The exact amount of anti-inflammatory agent to be used in the compositions will depend on the particular anti-inflammatory agent utilized since such agents vary widely in potency Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, oxicams such as piroxicam, salicylates such as aspirin; acetic acid derivatives, such as felbinac, fenamates, such as etofenamate, flufenamic, mefenamic, meclofenamic, acids; propionic acid derivatives, such as ibuprofen, naproxen, pyrazoles, and mixtures thereof. Mixtures of these non-steroidal anti-inflammatory agents may also be employed, as well as the dermatologically acceptable salts and esters of these agents.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (Kava Kava from SEDERMA (FR 2 771 002 and WO 99/25369), *Bacopa monieri* extract (Bacocalmine™ from SEDERMA, WO 99/40897) and sea whip extract, may be used. Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred. Additional anti inflammatory agents include diosgenol, saponines, sapogenins, lignanes, triterpenes saponosides and genines.

29) Tanning Actives

The compositions of the present invention can comprise a tanning active. In one embodiment, the composition comprises from about 0.1% to about 20%, more preferably from about 2% to about 7%, and even more preferably from about 3% to about 6%, by weight of the composition, of a tanning active. A preferred tanning active is dihydroxyacetone, which is also known as DHA or 1,3-dihydroxy-2-propanone. Especially useful are combinations with the tanning agents called Tyr-ol™ and Tyr-excel™ offered by SEDERMA and described in Fr 2 702 766 and WO 03/017966 respectively.

30) Skin Withening or Lightening Agents

The compositions of the present invention may contain a skin lightening agent. When used, the compositions preferably contain from about 0.01% to about 10%, more preferably from about 0.02% to about 5%, also preferably from about 0.05% to about 2%, by weight of the composition, of a skin lightening agent. Suitable skin lightening agents include those known in the art, including kojic acid, arbutin, tranexamic acid, ascorbic acid and derivatives thereof (e.g., magnesium ascorbyl phosphate or sodium ascorbyl phosphate, ascorbyl glucoside and the like), and extracts (e.g., mulberry extract, placental extract). Skin lightening agents suitable for use herein also include those described in WO95/34280, PCT/US95/07432, co-pending U.S. Ser. No. 08/390,152 and PCT/US95/23780. Especially useful are combinations with the skin lightening agents called Melaclear™, Etioline™, Melaslow™ and Lumiskin™ offered by SEDERMA and described respectively in FR 2 732 215, WO 98/05299, WO 02/15871 and PCT/FR 03/02400. Other skin lightening materials suitable for use herein can include Actiwhite® (Cognis), Emblica® (Rona), Azeloglicina (Sinerga) and Sepiwhite® (Seppic). A preferred skin lightening agent is ascorbyl glucoside.

31) Antimicrobial, Antibacterial and Antifungal Actives

The compositions of the present invention can comprise one or more anti-fungal or anti-microbial actives. A safe and effective amount of an antimicrobial or antifungal active can be added to the present compositions. In one embodiment, the composition comprises from about 0.001% to about 10%, preferably from about 0.01% to about 5%, and more preferably from about 0.05% to about 2%, by weight of the composition, of an antimicrobial or antifungal active.

Suitable anti-microbial actives include coal tar, sulfur, whitfield's ointment, castellani's paint, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazolinone and azoles, and combinations thereof. Preferred anti-microbials include itraconazole, ketoconazole, selenium sulphide and coal tar. In one embodiment, one or more anti-fungal or anti-microbial active is combined with an anti-dandruff active selected from polyvalent metal salts of pyrithione.

a) Azoles

Azole anti-microbials include imidazoles such as benzimidazole, benzothiazole, bifonazole, butoconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein are ketoconazole and climbazole.

b) Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5 c) Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d) Additional Anti-Microbial Actives

Additional anti-microbial actives of the present invention may include one or more keratolytic agents such as salicylic acid, extracts of melaleuca (tea tree) and charcoal. The present invention may also comprise combinations of antimicrobial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Preferred examples of actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neomycin sulfate, and mixtures thereof.

Especially useful are combinations with the ingredient range called OSMOCIDE™ offered by SEDERMA (WO 97/05856).

32) Thickening Agents (Including Thickeners and Gelling Agents)

The compositions of the present invention can comprise one or more thickening agents. In one embodiment, a thickening agent is present at a level of from about 0.05% to about 10%, preferably from about 0.1% to about 5%, and more preferably from about 0.25% to about 4%, by weight of the composition. Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, U.S. Pat. No. 4,509,949, U.S. Pat. No. 2,798,053, and in CTFA International Cosmetic Ingredient Dictionary, Tenth Edition, 2004. Examples of commercially available carboxylic acid polymers useful herein include the carbomers, which are homopolymers of acrylic acid crosslinked with allyl ethers of sucrose or pentaerythritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerythritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, U.S. Pat. No. 4,849,484, U.S. Pat. No. 4,835,206, U.S. Pat. No. 4,628,078, U.S. Pat. No. 4,599,379 and EP228868.

c) Polyacrylamide Polymers

The compositions of the present invention can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties and may be used in concentration ranges between 1 and 99%, most advantageously between 5 and 15%.

d) Polysaccharides

A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

33) Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, when antiperspirant actives are present in the compositions of the instant invention, the compositions comprise from about 0.01% to about 50%, more preferably from about 0.1% to about 40%, and still more preferably from about 1% to about 30%, by weight of the composition, of the antiperspirant compound.

34) Detersive Surfactants

The compositions of the present invention can include detersive surfactant from about 1% to about 90%, more preferably from about 5% to about 10%. The detersive surfactant component can be included to provide cleaning performance to the composition. The detersive surfactant component in turn can comprise anionic detersive surfactant, zwitterionic or amphoteric detersive surfactant, or a combination thereof. Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, and generally can range from about 5% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. Other suitable anionic detersive surfactants are the water-soluble salts of organic, sulfuric acid reaction products, alkoyl isethionates, sodium or potassium salts of fatty acid amides of methyl tauride, olefin sulfonates, beta-alkyloxy alkane sulfonates.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. No. 5,104,646 and U.S. Pat. No. 5,106,609.

Amphoteric detersive surfactants include derivatives of aliphatic secondary and tertiary amines.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. No. 3,929,678, U.S. Pat. No. 2,658,072, U.S. Pat. No. 2,438,091 and U.S. Pat. No. 2,528,378.

35) Cationic, Anionic and Amphoteric Polymers

The compositions of the present invention can comprise polymers which may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic When included, concentrations of the cationic polymer in the composition can typically range from about 0.05% to about 3%, preferably from about 0.075% to about 2.0%, more preferably from about 0.1% to about 1.0 a) Cationic Polymers

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl (meth)acrylate, dimethylaminopropyl (meth)acrylate, or dimethylaminopropyl (meth)acrylamide Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. A non limiting example is polymethyacrylamidopropyl trimonium chloride, available under the trade name Polycare 133, from Rhone-Poulenc.

Other suitable cationic polymers for use in the composition include polysaccharide polymers, such as cationic cellulose derivatives and cationic starch derivatives.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962, 418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

b) Anionic Polymers

Examples of anionic polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

c) Amphoteric Monomers

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth) acrylamide, as discussed above, modified with propanesultone.

36) Nonionic Polymers

The compositions herein can comprise nonionic polymers. For instance, polyalkylene glycols having a molecular weight of more than about 1000 can be used. Preferred polyethylene glycol polymers can include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl (meth)acrylate, methoxy ethyl (meth)acrylate, butoxyethyl (meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof

37) Hair Conditioning Agents

Conditioning agents include any material which is used to give a particular conditioning benefit to keratinous tissue. For instance, in hair treatment compositions, suitable conditioning agents include those which deliver one or more benefits relating to shine, softness, combability, antistatic properties, wet-handling, damage, manageability, body, and greasiness. Conditioning agents useful in the compositions of the present invention can comprise a water insoluble, water dispersible, non-volatile liquid that forms emulsified, liquid particles. Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When included, the concentration of the conditioning agent in the composition can be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a) Silicones

The conditioning agent of the compositions of the present invention is preferably an insoluble silicone conditioning agent. The silicone conditioning agent particles may comprise volatile silicone, non-volatile silicone, or combinations thereof. Non-volatile silicon conditioning agents are preferred. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989).

b) Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

c) Amino and Cationic Silicones

Cationic silicone fluids suitable for use in the compositions of the present invention include, but are not limited to, the polymer known as "trimethylsilylamodimethicone".

Other silicone cationic polymers which may be used in the compositions of the present invention may be UCARE SILICONE ALE 56™, available from Union Carbide.

d) Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

e) High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. No. 2,826,551, U.S. Pat. No. 3,964,500, U.S. Pat. No. 4,364,837, GB849433, and Silicon Compounds, Petrarch Systems, Inc. (1984).

f) Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

38) Organic Conditioning Oils

Compositions of the present invention may also comprise organic conditioning oil. In one embodiment, from about 0.05% to about 20%, preferably from about 0.08% to about 1.5%, more preferably from about 0.1% to about 1%, of at least one organic conditioning oil is included as a conditioning agent, either alone or in combination with other conditioning agents, such as the silicones (described herein).

a) Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation, hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b) Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of C4 to about C14 olefenic monomers, preferably from about C6 to about C12.

Preferred non-limiting examples of olefenic monomers for use in preparing the polyolefin liquids herein include ethylene, propylene, 1-butene, 1-pentene, 1-hexene to 1-hexadecenes, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

c) Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of C4 to C8 dicarboxylic acids (e.g. C1 to C22 esters, preferably C1 to C6, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as C10 to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters.

Specific non-limiting examples of suitable synthetic fatty esters for use in the compositions of the present invention include: P-43 (C8-C10 triester of trimethylolpropane), MCP-684 (tetraester of 3,3 diethanol-1,5 pentadiol), MCP 121 (C8-C10 diester of adipic acid), all of which are available from Mobil Chemical Company.

39) Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts, especially 1-hydroxy-2-pyridinethione salts. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"). Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753 and U.S. Pat. No. 4,470,982.

40) Humectant

The compositions of the present invention may contain a humectant. Humectants can be selected from the group consisting of polyhydric alcohols, water soluble alkoxylated nonionic polymers, and mixtures thereof. Humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

41) Suspending Agent

The compositions of the present invention may further comprise a suspending agent, preferably at concentrations effective for suspending water-insoluble material in dispersed form in the compositions or for modifying the viscosity of the composition. Such concentrations can preferably range from about 0.1% to about 10%, more preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, long chain acyl derivatives and mixtures thereof. These suspending agents are described in U.S. Pat. No. 4,741,855. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® available from Rheox, Inc Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

42) Terpene Alcohol

The compositions of the present invention may comprise a terpene alcohol or combinations of terpene alcohols. As used herein, "terpene alcohol" refers to organic compounds composed of two or more 5-carbon isoprene units [CH2=C(CH3)-CH=CH2] with a terminal hydroxyl group. Preferably, the composition can comprise from about 0.001% to about 50%, preferably from about 0.01% to about 20%, more preferably from about 0.1% to about 15%, even more preferably from about 0.1% to about 10%, still more preferably from about 0.5% to about 5%, and still more preferably from about 1% to about 5%, by weight of the composition, of the terpene alcohol.

Examples of terpene alcohols that can be useful herein include farnesol, derivatives of farnesol, isomers of farnesol, geraniol, derivatives of geraniol, isomers of geraniol, phytantriol, derivatives of phytantriol, isomers of phytantriol, and mixtures thereof. A preferred terpene alcohol for use herein is farnesol.

a) Farnesol and Derivatives Thereof

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco) and trans-trans-farnesol (Sigma Chemical Company). A suitable derivative of farnesol is farnesyl acetate which is commercially available from Aldrich Chemical Company.

b) Geraniol and Derivatives Thereof

Geraniol is the common name for the chemical known as 3,7-dimethyl-2,6-octadien-1-ol. As used herein, "geraniol" includes isomers and tautomers of such. Geraniol is commercially available from Aldrich Chemical Company. Suitable derivatives of geraniol include geranyl acetate, geranylgeraniol, geranyl pyrophosphate, and geranylgeranyl pyrophosphate, all of which are commercially available from Sigma Chemical Company. For example, geraniol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

c) Phytantriol and Derivatives Thereof

Phytantriol is the common name for the chemical known as 3,7,11,15, tetramethylhexadecane-1,2,3,-triol. Phytantriol is commercially available from BASF. For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

43) Enzymes, Enzyme Inhibitors and Enzyme activators (Coenzymes)

The compositions of the present invention may contain a safe and effective amount of one or more enzymes, enzyme inhibitors or enzyme activators (coenzymes). Examples of enzymes are lipases, proteases, catalase, superoxide-dismutase, amylases, glucuronidases, peroxidases, in particular glutathione peroxidase or lactoperoxidase, ceramidases, hyaluronidases. All of these enzymes may be obtained by extraction or by fermentation biotechnology processes. Examples of enzyme inhibitors include trypsine inhibitors, Bowmann Birk inhibitor, chymotrypsin inhibitors, botanical extracts with or without tannins, flavonoids, quercetin which inhibit enzymatic activity. Enzyme preparations can be found, for instance, in the product named VENUCEANE proposed by SEDERMA, France (WO 02/066668). Enzyme activators and coenzymes include Coenzyme A, coenzyme Q10 (ubiquinone), glycyrrhizidine, berberine, chrysine.

II CARRIER

The compositions of the present invention can comprise an orally or a deimatologically acceptable carrier, or injectible liquid, depending upon the desired product form.

A. Dermatologically Acceptable Carrier

The topical compositions of the present invention can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition.

The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition. In one embodiment, oil-in-water emulsions are especially preferred.

Emulsions according to the present invention can contain an aqueous phase and a lipid or oil. Lipids and oils may be derived from animals, plants, or petroleum and may be natural or synthetic (i.e., man-made). Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421, 769, and McCutcheon's Detergents and Emulsifiers, North American Edition, pages 317-324 (1986). Suitable emulsions may have a wide range of viscosities, depending on the desired product form.

The compositions of the present invention can be in the form of pourable liquids (under ambient conditions). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The emulsion may also contain an anti-foaming agent to minimize foaming upon application to the keratinous tissue. Anti-foaming agents include high molecular weight silicones and other materials well known in the art for such use.

Preferred water-in-silicone and oil-in-water emulsions are described in greater detail below.

1) Water-in-Silicone Emulsion

Water-in-silicone emulsions contain a continuous silicone phase and a dispersed aqueous phase.

a) Continuous Silicone Phase

Preferred water-in-silicone emulsions of the present invention contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the active ingredients of the present invention. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid, Dow Corning® 225 fluid, and Dow Corning® 200 fluids Examples of suitable alkyl-substituted dimethicones include cetyl dimethicone and lauryl dimethicone.

Cyclic polyalkylsiloxanes suitable for use in the composition include commercially available cyclomethicones such as Dow Corning® 244 fluid, Dow Corning® 344 fluid, Dow Corning® 245 fluid and Dow Corning® 345 fluid.

Also useful are materials such as trimethylsiloxysilicate. A commercially available trimethylsiloxysilicate is sold as a mixture with dimethicone as Dow Corning® 593 fluid.

Dimethiconols are also suitable for use in the composition. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

b) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

c) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Dimethicone copolyol emulsifiers useful herein are described, for example, in U.S. Pat. No. 4,960,764, European Patent No. EP 330,369, Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. No. 5,011,681; U.S. Pat. No. 4,421,769; and U.S. Pat. No. 3,755,560

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

d) Silicone Elastomer

The compositions of the present invention also include from about 0.1% to about 30%, by weight of the composition, of a silicone elastomer component. Preferably, the composition includes from about 1% to about 30%, more preferably from about 2% to about 20%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from: a) an organopolysiloxane having at least 2 lower alkenyl groups in each molecule; b) an organopolysiloxane having at least 2 silicon-bonded hydrogen atoms in each molecule; and c) a platinum-type catalyst.

The compositions of the present invention may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793, and 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252, U.S. Pat. No. 5,760,116 and U.S. Pat. No. 5,654,362.

Commercially available elastomers preferred for use herein are Dow Corning's 9040 silicone elastomer blend, Shin Etsu's KSG-21, and mixtures thereof.

e) Carrier for Silicone Elastomer

The topical compositions of the present invention may include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Concentrations of the carrier in the cosmetic compositions of the present invention will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 (cal/cm3>)05.

f) Non-Polar, Volatile Oils

The composition of the present invention may include non-polar, volatile oils. The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

g) Relatively Polar, Non-Volatile Oils

The composition of the present invention may include relatively polar, non-volatile oils. The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present invention are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

h) Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, and mixtures thereof.

2) Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include nonionic, anionic, cationic, and amphoteric emulsifiers. Non-limiting examples of emulsifiers useful in the oil-in-water emulsions of this invention are given in McCutcheon's, Detergents and Emulsifiers, North American Edition (1986), U.S. Pat. No. 5,011,681, U.S. Pat. No. 4,421,769 and U.S. Pat. No. 3,755,560. Examples of suitable oil-in-water emulsion carriers are described in U.S. Pat. No. 5,073,371 and U.S. Pat. No. 5,073,372. An especially preferred oil-in-water emulsion, containing a structuring agent, hydrophilic surfactant and water, is described in detail hereinafter.

a) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

b) Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula (S)n-O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids), the condensation products of alkylene oxides with 2 moles of fatty acids (i.e. alkylene oxide diesters of fatty acids), the condensation products of alkylene oxides with fatty alcohols (i.e. alkylene oxide ethers of fatty alcohols), the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants, An especially preferred surfactant corresponding to the above structure is coconut alkyl N-methyl glucoside amide. Processes for making compositions containing polyhydroxy fatty acid amides are disclosed, for example, U.S. Pat. No. 2,965,576; U.S. Pat. No. 2,703,798, and U.S. Pat. No. 1,985,424.

Preferred among the nonionic surfactants are those selected from the group consisting of steareth-21, ceteareth-20, ceteareth-12, sucrose cocoate, steareth-100, PEG-100 stearate, and mixtures thereof. Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, Detergents & Emulsifiers, (North American edition 1979) M.C. Publishing Co.; and Schwartz, et al., Surface Active Agents, Their Chemistry and Technology, New York: Interscience Publishers, 1949.

Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethianonic acid and neutralized, i.e. the alkoyl isethionates typically have the formula RCO—OCH2CH2SO3M wherein R is alkyl or alkenyl of from about 10 to about 30 carbon atoms, and M is a water-soluble cation such as ammonium, sodium, potassium and triethanolamine. For example, the fatty acids are derivated from coconut or palm kernel oil. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. Other similar anionic surfactants are described in U.S. Pat. Nos. 2,486,921; 2,486,922 and 2,396,278.

The alkyl and alkyl ether sulfates typically have the respective formulae ROSO3M and RO(C2H40)xSO3M, wherein R is alkyl or alkenyl of from about 10 to about 30 carbon atoms, x is from about 1 to about 10, and M is a water-soluble cation such as ammonium, alkanolamines such as triethanolamine, monovalent metals, such as sodium and potassium, and polyvalent metal cations such as magnesium and calcium. Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized Another suitable class of anionic surfactants are the water-soluble salts of the organic, sulfuric acid reaction products of the general formula:

wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions is the beta-alkyloxy alkane sulfonate class. These surfactants conform to the formula

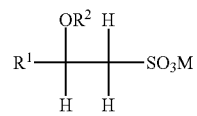

where R1 is a straight chain alkyl group having from about 6 to about 20 carbon atoms, R2 is a lower alkyl group having from about 1 to about 3 carbon atoms, preferably 1 carbon atom, and M is a water-soluble cation as described hereinbefore. Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH(CH2)mCO2M wherein m is from 1 to 4, R is a C8-C22 alkyl or alkenyl, and M is H, alkali metal, alkaline earth metal ammonium, or alkanolammonium. Preferred amphoteric surfactants for use in the present invention include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072; N-higher alkyl aspartic acids such as those produced according to the teaching of U.S. Pat. No. 2,438,091; and the products sold under the trade name "Miranol" and described in U.S. Pat. No. 2,528,378. Other examples of useful amphoterics include phosphates, such as coamidopropyl PG-dimonium chloride phosphate (commercially available as Monaquat PTC, from Mona Corp.).

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

c) Water Emollient

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80%, water; the actives and the additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72-73 (1972), and/or an emollient. For example, an ointment may contain from about 2% to about 10% of an emollient; from about 0.1% to about 2% of a thickening agent as well as the active ingredient(s) and the additional ingredient(s) in the above described amounts.

Compositions of this invention useful for cleansing ("cleansers") can be formulated with a suitable carrier, e.g., as described above, and preferably comprise from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, for exemplary surfactants useful herein. Examples of a broad variety of additional surfactants useful herein are described in McCutcheon's Detergents and Emulsifiers, North American Edition (1986), published by Allured Publishing Corporation. The cleansing compositions can optionally contain, at their art-established levels, other materials which are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example in PCT Application WO 96/33689, and U.K. Patent GB 2274585.

B. Orally Acceptable Carrier

The compositions of the present invention can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, syrups, granules, powders, vitamins, supplements, health bars, candies, chews, and drops.

C. Injectible Liquid

The compositions of the present invention can also comprise a liquid that is acceptable for injection in and/or under the skin if the composition is to be injected. Any suitable acceptable liquid as known in the art or otherwise can be used.

III. COMPOSITION PREPARATION

The compositions of the present invention are generally prepared by conventional methods such as are known in the art of making topical and oral compositions and compositions for injection. Such methods can typically be conducted in one or more steps, with or without heating, cooling, and the like.

The physical form of the compositions according to the invention is not important: they may be in any galenic form such creams, lotions, milk or cream ointments, gels, emulsions, dispersions, solutions, suspensions, cleansers, foundations, anhydrous preparations (sticks, in particular lipbalm, body and bath oils), shower and bath gels, shampoos and scalp treatment lotions, cream or lotion for care of skin or hair, make-up removing lotions or creams, sun-screen lotions, milks or creams, artificial suntan lotions, creams or milks, pre-shave, shave or aftershave creams, foams, gels or lotions, make-up, lipsticks, mascaras or nail varnishes, skin "essences," serums, adhesive or absorbent materials, transdermal patches, or powders, emollient lotion, milk or cream, sprays, oils for the body and the bath, foundation tint bases, pomade, emulsion, colloid, compact or solid suspension, pencil, sprayable or brossable formulation, blush, red, eyeliner, lipliner, lip gloss, facial or body powder, styling foams or gels, nail conditioner, lip balms, skin conditioners, moisturizers, hair sprays, soaps, body exfoliants, astringents, depilatories and permanent waving solutions, antidandruff formulations, anti-sweat and antiperspirant compositions, nose sprays and so on. These compositions can also be presented in the form of lipsticks intended to apply colour or to protect the lips from cracking, or of make-up products for the eyes or tints and tint bases for the face. Compositions in accordance with the invention include cosmetics, personal care products and pharmaceutical preparations. The present invention may also be applied on animal skin and/or appendages. One can also consider a composition in the shape of foam or in the form of compositions for aerosol also including a propellant agent under pressure.

Cosmetic compositions according to the invention may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

Oridonin or the combination of oridonin and darutigenol or the combination of oridonin and darutoside according to the present invention may be in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, micro or nano emulsions or adsorbed on organic polymer powders, talcs, bentonites, or other inorganic or organic supports.

Oridonin or the combination of oridonin and darutigenol or the combination of oridonin and darutoside according to the present invention may be used in any form whatsoever, in a form bound to or incorporated in or absorbed in or adsorbed on macro-, micro-, and nanoparticles, or macro-, micro-, and nanocapsules, for the treatment of textiles, natural or synthetic fibres, wools, and any materials that may be used for clothing or underwear for day or night intended to come into contact with the skin, handkerchiefs or cloths, to exert their cosmetic effect via this skin/textile contact and to permit continuous topical delivery.

IV. METHOD OF COSMETIC TREATMENT

The present invention also relates to a method of cosmetic treatment to improve the general condition of the skin, comprising applying topically to the skin an effective amount of oridonin or a composition of oridonin and darutigenol or a combination of oridonin and darutoside, as defined above, in particular:

to prevent and/or treat the signs of skin ageing;

to prevent and/or treat skin sagging, and/or improve the tone, and/or firmness and/or elasticity of the skin;

to prevent and/or treat skin atrophy, and/or improve the density of the dermis and epidermis;

to give or restore volume to the dermis and epidermis;

to prevent and/or treat skin dehydration;

to prevent and/or treat skin roughness;

to prevent and/or treat cellulite, to reduce the expansion and/or prevent the development of adipose tissue in the hypodermis;

to prevent and/or treat glycation of molecules in the skin;

to prevent and/or treat acne;

to prevent and/or treat skin breakdown due to the effects of oxidation;

to prevent and/or treat inflammatory conditions.

The composition according to the invention can be applied locally onto areas of the face, lips, neck, neckline, hands, feet or body. One of the major advantages of the present invention is the possibility of being able to perform whenever necessary or desirable, "gentle", highly localised selective treatments using the topical non invasive method of application.

In the case of an anti-wrinkle use for example, the application can be achieved in a very localized manner using a syringe or a microcannula.

It is however possible to consider a composition according to the invention intended to be injected subcutaneously.

According to the invention, it is possible to propose several compartment devices or kits for implementing the process described above, which could include, for example, and without limitation, a first compartment containing a composition of oridonin and a second compartment containing a composition of another ingredient, darutigenol or darutoside for example, and/or excipients, the compositions contained in said first and second compartments being considered here as a composition combination for a simultaneous, separate in time or sequential use in one of the treatments defined above.

According to other features, the method of treatment of the invention can be combined with one or more other methods of skin treatment, such as light therapy, aromatherapy or heat treatments.

The invention also proposes a method in which the compound of the invention is the active agent of cosmeceutical or nutraceutical composition orally administered.

V. EXAMPLES

The following examples describe and demonstrate various aspects whithin the scope of the present invention. The examples are given solely for purposes of illustration and should not be construed as a limitation of the present invention. Also by way of illustration, several cosmetic formulations are listed. The formulations are representative of the invention, but do not restrict it.

A—IN VITRO STUDIES

Darutoside used in the Studies is the darutoside molecule, commercially available under the trade name Darutigenol™.

The tested products are:
pure oridonin used at the following concentrations:
  1.5 ppm, 3 ppm and 4.5 ppm;
pure darutoside used at the following concentrations:
  5 ppm, 10 ppm and 15 ppm;
A combination of oridonin and darutoside and used at the following concentrations:
  1.5 ppm of oridonin and 5 ppm of darutoside;
  3 ppm of oridonin and 10 ppm of darutoside;
  4.5 ppm of oridonin and 15 ppm of darutoside.

1. Fighting Oxidative Stress a. Reduction in Peroxyl Radicals: ORAC Test

The Oxygen-Radical Absorbance Capacity (ORAC) test is a method enabling evaluation of the antioxidant capability of molecules and extracts of plant origin. A free radical generator (peroxyl radical) is placed in contact with a substrate revealing free radical presence: fluorescein. The free radical-induced dimerization of fluorescein decreases its fluorescence. The antioxidant molecules will reduce this degradation Results:

TABLE 1

Action of oridonin and of a combination of oridonin and darutoside on the reduction of the destruction of fluorescein by free radicals. (n = 6).

| Concentration of oridonin | 1.5 ppm | 3 ppm | 4.5 ppm |
| --- | --- | --- | --- |
| oridonin effect | +14%; p < 0.01 | +4%; dns | −4%; dns |
| Concentrations of oridonin and darutoside | 1.5 ppm of oridonin + 5 ppm of darutoside | 3 ppm of oridonin + 10 ppm of darutoside | 4.5 ppm of oridonin + 15 ppm of darutoside |
| Effect of oridonin and darutoside | −15%; p < 0.01 | −24%°; p < 0.01 | −33%; p < 0.01 | dns = non significative difference/control b. Evaluation of the Antioxidation Power of the Ordionin/Darutoside Combination: ROS on Human Dermal Fibroblasts (DCFH-DA Method)

Human dermal fibroblasts are placed in contact to the oridonin/darutoside combination during 24 h, then in contact with the DCFH-DA probe (2,7'-dichlorofluorescein diacetate). This probe, when it has been metabolized in the cell, becomes sensitive to the redox status of the cell. Cells are then exposed to oxidative stress with hydrogen peroxide.

After rinsing, the fluorescence is determined in order to compare the residual oxidation level of the cells with oridonin and darutoside combination compared to that of the negative control (after LEBEL et al, 1992, modified).

Results:

TABLE 2

Effect of the ordinonin/darutoside combination on the reduction of intracellular oxidation.

| UFA/wells means | | Concentration of oridonin and darutoside respectively: | | |
| --- | --- | --- | --- | --- |
| (N = 7 tests/case) | Control | 1.5 ppm + 5 ppm | 3 ppm + 10 ppm | 4.5 ppm + 15 ppm |
| without $H_2O_2$ | 9226 | 8397 | 8478 | 7998 |
| 400 µM $H_2O_2$ | 16312 | 15376 | 14648 | 13652 |

(n = 7)

The decrease of intracellular oxidation is significant with $p<0.05$ at the concentrations of oridonin and of darutoside of respectively (3 ppm+10 ppm) and (4.5 ppm+15ppm).

c. Stimulation of Reduced Glutathione (GSH) Synthesis

Human keratinocytes at confluence are exposed 24 h to tested products. Intracellular GSH concentration was determined by ELISA.

TABLE 3

Effect of oridonin and of the combination of oridonin and darutoside on stimulation of intracellular GSH synthesis (n = 6).

| | Concentration | GSH change as % of control |
| --- | --- | --- |
| oridonin | 3 ppm | +41%; p < 0.01 |
| | 4.5 ppm | +79%; p < 0.01 |
| darutoside | 10 ppm | +3%; dns |
| | 15 ppm | +2%; dns |
| oridonin and darutoside combination | 3 ppm + 10 ppm | +48%; p < 0.01 |
| | 4.5 ppm + 15 ppm | +90%; p < 0.01 |

2. Strengthening of the Chromophore Collagen a. Induction of Collagen I Synthesis The stimulation of collagen I synthesis was evaluated by image analysis of immunolabeled human dermal fibroblast layers following exposure to various concentrations of oridonin and darutoside.

Results:

TABLE 4

Change in the production of Collagène I with oridonin and darutoside.

| | Concentrations respectively of oridonin and darutoside | Collagen I AFU/$10^6$ cell. | % change; significance |
|---|---|---|---|
| Control | — | 7.35 ± 2.91 | Reference |
| oridonin and darutoside | 1.5 ppm + 5 ppm | 10.64 ± 5.30 | +45%; p < 0.06 |
| | 3 ppm + 10 ppm | 17.14 ± 7.47 | +133%; p < 0.01 |
| | 4.5 ppm + 15 ppm | 19.87 ± 9.98 | +170%; p < 0.01 |

AFU: arbitrary fluorescence unit (n = 5); No toxic effect was observed after 19 days of exposure.

b. Retriggering of Collagen I and III Synthesis; Aged Skin Model

Reconstructed skin (Full Thickness Skin, Phenion) was experimentally aged using a topical corticosteroid (betamethasone), which reduced collagen synthesis by the fibroblasts and thus weakened the structure of the dermal fibers. About 8 h after exposure, the combination oridonin (4.5 ppm) and darutoside (15 ppm) was applied to the surface of the skin specimens (n=3) daily for 4 days. In parallel, oridonin and darutoside free placebo was applied to the control skin specimens.

The skin specimens were frozen and sectioned. The sections were immunolabeled to monitor collagen I and collagen III. An analysis of the variations was conducted on the microscope images.

Results:

TABLE 5

Variation of collagen I and III production after 4 days of oridonin and darutoside application

| | Coll. I (AFU) | % change Coll. I | % change Coll. I | Coll. III (AFU) | % change Coll. III | % change Coll. III |
|---|---|---|---|---|---|---|
| Non-aged control | 26.8 ± 7.3 | Ref. 1 | — | 25.5 ± 5.2 | Ref. 1 | — |
| Aged skin + placebo | 20.4 ± 4.8 | −21%; p < 0.06 | Ref. 2 | 17.2 ± 3.9 | −33%; p < 0.01 | Ref. 2 |
| Aged skin + oridonin 4.5 ppm and Darutigenol ™ 15 ppm | 26.3 ± 4.9 | +2%; dns | +29%; p < 0.05 | 22.4 ± 5.0 | −12%; dns | +31%; p < 0.05 |

AFU: arbitrary fluorescence unit

As expected, the results show that, for the experimentally aged skin specimens, collagen I and III syntheses were markedly reduced (−21 and −33%, respectively) vs. the non-aged control specimen. The use of oridonin and darutoside combination enabled maintenance of a "normal" state since the collagen labeling was similar to that of the non-aged control.

c. Reduction in MMP-1 Synthesis

Dermal human fibroblasts were exposed to the combination oridonin+darutoside for 48 h. Following exposure, the MMP-1 present in the culture medium was assayed by ELISA.

Results:

TABLE 6

Change in MMP-1 production in the presence of oridonin and darutoside

| | Concentration | MMP-1 (ng/$10^6$ cells) | % change; significance |
|---|---|---|---|
| Control | — | 1156 +/− 100 | Reference |
| oridonin and darutoside | 3 ppm + 10 ppm | 956 +/− 66 | −17%; p < 0.05 |
| | 4.5 ppm + 15 ppm | 658 +/− 112 | −43%; p < 0.01 |

(n = 3)

The results obtained on the chromophore, collagen, showed that a combination of oridonin and darutoside is endowed with the property of intensifying collagen synthesis, including in experimentally aged skin, and limiting the degradation of the matrix by repressing MMP-1 formation (−43% with 4.5ppm of oridonin+15 ppm of darutoside).

3. Action on the Red Chromophore a. Change in VEGF Synthesis

Cultured human keratinocytes were exposed to the products to be tested for 24 h. The cells were then subjected to UVB irradiation in buffer and then again exposed to the products for 24 h. After exposure, VEGF was determined by ELISA.

Results:

TABLE 7

Change in VEGF production in the presence of the combination of oridonin and darutoside

| | Concentration | VEGF change in control %; significance |
|---|---|---|
| oridonin and darutoside combination | 3 ppm + 10 ppm | −47%; p < 0.01 |

(n = 4)

b. Evaluation of the Anti-Redness Effect: Het-CAM Method

The Het-CAM model is recommended as an alternative method for the evaluation of the irritant effect of cosmetics. The model uses eggs at a very early stage of development since the nervous system is not yet fully developed (JORF No. 300, Dec. 26, 1996).

A moderately irritant product induces instantaneous changes in the capillary density of the chorioallantoic membrane. Previously invisible blood vessels become clearly visible under the effect of vasodilatation. This property was exploited to evaluate the effect of the combination of oridonin and darutoside.

The combination oridonin+darutoside was applied to the surface of the chorioallantoic membrane and, after incubation, a surfactant, used as an SDS irritant agent, in an appropriate concentration, was applied to the surface of the membrane.

A score was determined by an experienced operator and compared to that for the membranes exposed to the irritant alone (negative control) and that for the membranes exposed to aspirin, used as the positive control (JORF published method, modified).

Results:

TABLE 8

Change in inflammation index in the presence of 3% of the combination of oridonin and darutoside

|  | Control (Irritant alone) | Concentrations of oridonin and darutoside respectively: 4.5 ppm + 15 ppm | 5000 ppm aspirin |
|---|---|---|---|
| Mean score | 10 +/− 1.63 Reference | 4 +/− 2.12 p < 0.01 | 2 +/− 2.06 p < 0.01 |

The scores obtained showed that inflammation was very markedly slowed by aspirin and contained by the combination of oridonin and darutoside.

c. Change of the Inflammation

Cultured human fibroblasts were exposed to the products to be tested for 24 h. Then the cells were UVB irradiated in a buffer and exposed again to the contact of the products for 24 h. After exposure, PGE2, IL6 and IL8 presence were evaluated by ELISA.

Results:

TABLE 9

Change in the PGE2, IL6 & IL8 production

|  | Concentration | PGE2 change in control % | IL6 change in control % | IL8 change in control % |
|---|---|---|---|---|
| oridonin and darutoside | 1.5 ppm + 5 ppm | −46%; p < 0.01 | −44%; p < 0.01 | −48%; p < 0.01 |

(n = 4)

4. Action on the Chromophore Melanin i. Change in the Ability to Phagocyte Melanosomes Cultured human keratinocytes were exposed to the combination of oridonin and darutoside for 48 h. Fluorescent melanosome models were then added to the cells for phagocytosis. Intracellular fluorescence was then determined using a fluorescence reader (n=12).

Results:

TABLE 10

Change in keratinocyte melanosome phagocytosis in the presence of 3% of the combination of oridonin and darutoside

|  | Concentrations | Phagocytosis (AFU/$10^4$ cells) | % change; significance |
|---|---|---|---|
| Control | — | 5996 +/− 792 | Reference |
| oridonin and darutoside | 3 ppm + 10 ppm | 4640 +/− 875 | −23%; p < 0.01 |
|  | 4.5 ppm + 15 ppm | 3973 +/− 497 | −34%; p < 0.01 |

AFU: Arbitrary fluorescence unit

The combination oridonin and darutoside thus reduced, in a dose-dependent manner, the ability of keratinocytes to phagocyte melanosomes.

ii. Change in the Dendricity of Melanocytes

Human melanocytes were exposed to media conditioned with human keratinocytes exposed to the combination of oridonin and darutoside for 48 h. These media were recovered and putted for 48 h on a human melanocyte culture, then the layers were fixed and the cells observed.

Using an image analysis software, the number and length of the dentrite were determined (n=150 cells/case).

Results:

TABLE 11

Change in the melanocyte dendricity in presence of the combination oridonin and darutoside

|  | Control | Concentrations of oridonin 3 ppm and of darutoside 10 ppm |
|---|---|---|
| Mean number of dendrite/cell | 2.6 ± 0.9 | 2.5 ± 0.8 |
| Mean length of dendrites | 25.6 μm ± 14.4 | 17.2 μm ± 11.3 |
| % Change; significance | Reference | −33%; p < 0.01 |

These results show that the average total number of dendrites is not significantly reduced by the combination oridonin and darutoside.

However the length of dendrites, and thus the ability of melanocytes to transfer their melanosomes, is reduced by 33% (p<0.01).

iii. Change in the Melanogenesis of Human Melanocytes in Monolayer

Human melanocytes were cultured and exposed with the test products for 5 days. After incubation the melanin content was measured in cell homogenates (n=4).

TABLE 12

% Change/control (melanin content).

| Concentrations of oridonin and darutoside | oridonin | darutoside | oridonin and darutoside |
|---|---|---|---|
| 125 ppm of oridonin + 3.75 ppm of darutoside | −16%; p < 0.01 | +1%; dns | −25%; p < 0.01 |
| 5 ppm of oridonin + 5 ppm of darutoside | −21%; p < 0.01 | +2%; dns | −26%; p < 0.01 |
| 2.25 ppm of oridonin + 7.5 ppm of darutoside | −23%; p < 0.01 | −4%; dns | −36%; p < 0.01 |
| 3 ppm of oridonin + 10 ppm of darutoside | −34%; p < 0.01 | −7%; p < 0.05 | −45%; p < 0.01 |

5. Slimming

Human preadipocytes are cultured and induced to differentiate in the presence of oridonin. After 10 days of differentiation, G3PDH activity was measured in cell homogenates as a marker of differentiation. (n=4).

TABLE 13

| | Concentrations | Act G3PDH (mU/$10^6$ cell) | % Change; significance |
|---|---|---|---|
| Control | — | 220.2 +/− 32.8 | Reference |
| oridonin | 2.7 ppm | 162.1 +/− 31.4 | −26%; p < 0.05 |
| | 3.6 ppm | 127.7 +/− 19.2 | −42%; p < 0.01 |

A dose-dependent and significant decrease of the activity of G3PDH of human adipocytes in the presence of oridonin is observed compared to the nontreated case (control).

B—FORMULATION EXAMPLES a) Comprising Oridonin

Pa is a solution comprising between 0.00001% and 50% of oridonin. The preparation P1 is an embodiment of the invention. The amount of such preparation in a cosmetic composition can vary in a large extend.

Example P1

| Starting materials | Wt % |
|---|---|
| Water | 20.0000 |
| Butylen glycol | 79.9320 |
| oridonin* | 0.0180 |

*pure oridonin amount

Formulation n° 1: Anti-Wrinkle Day Cream

| Starting materials | CTFA name | % | % |
|---|---|---|---|
| Phase A | | | |
| H₂O | | Qsp100 | Qsp100 |
| Ultrez 10 | Carbomer | 0.10 | 0.10 |
| Phase B | | | |
| P1 | | 3.00 | 3.00 |
| Phase C | | | |
| Dermaxyl ™ | | — | 2.00 |
| Volpo S 2 | Steareth 2 | 0.60 | 0.60 |
| Crodafos CES | Cetearyl alcohol dicetyl phosphate & Ceteth-10 phosphate | 4.00 | 4.00 |
| Crodamol STS | PPG-3 Benzyl Ether Myristate | 2.00 | 2.00 |
| Crodamol OSU | Dioctyl Succinate | 7.00 | 7.00 |
| Crill 3 | Sorbitan Stearate | 1.60 | 1.60 |
| Nipagine | Methyl Paraben | 0.30 | 0.30 |
| Phase D | | | |
| Potassium sorbate | Potassium Sorbate | 0.10 | 0.10 |
| Phase E | | | |
| NaOH 30% | Sodium Hydroxide | 0.35 | 0.35 |
| H₂O | | 3.50 | 3.50 |
| Phase F | | | |
| Fragrance | | 0.10 | 0.10 |

Dermaxyl ™ is a product of Sederma (WO2004/101609): an anti-ageing agent comprising the association of ceramide 2, the stratum corneum cement and the palmitoylated matrikine Pal-Val-Gly-Val-Ala-Pro-Gly. Dermaxyl ™ stimulates cell communication and then repairs the age related skin damage. The presence of Dermaxyl ™ in the cream reinforces the anti-ageing properties of the oridonin ingredient of the present invention.

Operating Procedure:

Phase A: Powder Ultrez 10 in water. Leave for swelling 20 minutes. Then weigh and heat phase B until dissolution. Add phase B in phase A. Weigh phase C. Heat phase A+B and phase C at 80° C. under water-bath. Under stirring, pour phase C into phase A+B. Homogenize, then add phase D. Homogenize, then add phase E around 50° C. Add phase F around 35° C.

Formulation n° 2: Anti-Ageing Tightener Gel

| Starting materials | CTFA name | % |
|---|---|---|
| Phase A | | |
| Natrosol 250M | Hydroxyethyl cellulose | 2.00 |
| Jaguar HP 105 | Guar gum | 0.70 |
| H₂O | | Qsp100 |
| Sorbate de potassium | Potassium Sorbate | 0.10 |
| Phase B | | |
| Pure oridonin | | 0.05 |
| Nipagine | Methyl paraben | 0.20 |
| Glycerin | Glycerin | 40.00 |
| Phase C | | |
| H₂O | | 8.00 |
| Ultrez 10 | Carbomer | 0.40 |
| Phase D | | |
| NaOH 30% | Sodium hydroxide | 0.40 |
| H₂O | | 4.00 |

-continued

| Starting materials | CTFA name | % |
|---|---|---|
| Phase E | | |
| Skin tightener ST ™ | | 10.00 |
| Phase F | | |
| Crillet 1 | Polysorbate 20 | 1.00 |
| Fragrance | Parfume | 0.10 |

Skin tightener ST ™ is a cosmetic ingredient of Sederma: it tightens and smoothes skin. It is an association of prolamines (wheat proteins with a very high molecular weight, very rich in glutamine/glutamic acid with polymannuronate (a hydrophilic polysaccharide from algae *Macrocystis pyrifera*).

Operating Procedure:

Weigh phase A. Let swell under stirring propeller v=300 rpm for 2 hours. Weigh phase B and heat until dissolved. Add phase B into phase A under normal stirring. Weigh phase C and let swell without stirring for ½ hour. Add phase C into phase A+B, mix well. Mix phase D then add into phase A+B+C. Stir blade 300 rpm. Then add phase E, mix well. Weigh and mix phase F. Then add phase F in the previous phase, mix well.

Formulation n° 3: Anti-Wrinkle and Anti-Rednesses Lotion

| Starting materials | CTFA name | % | % |
|---|---|---|---|
| Phase A | | | |
| H₂O | Water | Qsp100 | Qsp100 |
| Phase B | | | |
| Volpo G 26 | Glycereth 26 | 4.00 | 4.00 |
| Phenoxyethanol | Phenoxyethanol | 1.00 | 1.00 |
| Pure oridonin | | 0.05 | 0.05 |
| Phase C | | | |
| Crillet 1 | Polysorbate 20 | 2.00 | 2.00 |
| Verbena Fragrance | Fragrance | 0.10 | 0.10 |
| Phase D | | | |
| Phytotonine ™ | | — | 5.00 |

Phytotonine ™: is a cosmetic ingredient of Sederma: a concentrated hydroglycolic extract of *Arnica*, *Cypress* and *Solomon's Seal*. Phytotonine ™ reinforces vascular walls and improves microcirculation in veins and capillary vessels.

Operating Procedure:

Weigh phase A. Weigh phase B and heat until completely dissolved. Then add phase B into phase A, stir under propeller v=300 rpm. Weigh and mix phase C. Then add phase C into phase A+B, stir under propeller v=300 rpm. Then add the phase D in phase A+B+C. Homogenize under propeller, v=300 rpm.

Formulation n° 4: Slimming Cream

| Starting materials | CTFA name | % | % |
|---|---|---|---|
| Phase A | | | |
| Ultrez 10 | Carbomer | 0.40 | 0.40 |
| H₂O | | Qsp100 | Qsp100 |
| Phase B | | | |
| Pure Oridonin | | 0.05 | 0.05 |
| Nipagine | Methyl paraben | 0.20 | 0.20 |
| Glycerin | Glycerin | 10.00 | 10.00 |
| Phase C | | | |
| Natrosol 250M | Hydroxyethyl cellulose | 0.20 | 0.20 |
| Phase D | | | |
| Crillet 1 | Polysorbate 20 | 2.00 | 2.00 |
| Crodamol OP | EthylHexyl Palmitate | 4.00 | 4.00 |
| DC 200 | Dimethicone | 3.00 | 3.00 |
| Pemulen TR2 | Acrylates/10-30 Alkyl Acrylates cross polymer | 0.20 | 0.20 |
| Phase E | | | |
| Sorbate de potassium | Potassium Sorbate | 0.10 | 0.10 |
| Phase F | | | |
| NaOH 30% | sodium hydroxide | 0.60 | 0.60 |
| H₂O | | 6.00 | 6.00 |
| Phase G | | | |
| Ethanol 95 | Ethanol | 3.00 | 3.00 |
| Phase H | | | |
| Bodyfit ™ | | — | 2.50 |
| Phase I | | | |
| Fragrance | Fragrance | 0.10 | 0.10 |

Bodyfit ™: is a product of Sederma (WO2004/024695): it diminishes the appearance of cellulite and enhances skin firmness. It contains glaucine in a water-soluble excipient. Glaucine is a multifunctional molecule that stimulates lipolysis and inhibits the appearence of new adipocytes, by calcium flow regulation. Bodyfit ™ can reinforce the action of the slimming action of oridonin.

Operating Procedure:

Phase A: Sprinkle Ultrez 10 in water, let swell 30 minutes. Mix phase B and heat until dissolved. Add phase C into phase B and mix. Pour phase B+C in phase A under stirring propeller v=300 rpm. Let rise 1 hour. Then add phase D, under stirring propeller v=300 rpm. Add phase E extemporaneously, under stirring propeller v=300 rpm. Neutralize with phase F under stirring blade v=300 rpm. Add phase G, homogenize. Add phase H and then phase I, homogenize at the end. Chek pH +/−6.00.

b) Comprising Oridonin and Darutoside or Darutigenol

Pb is a solution comprising between 0.00001% and 50% and 0.00001% of oridonin and 0.00001% and 80% of darutoside (sold under the commercial name Darutigenol™).

Preparation P2 is an embodiment of the invention. The amount of such a preparation in a cosmetic composition can vary in a large extend.

Example P2

| Ingredients | Wt % |
|---|---|
| Water | 20.0000 |
| Butylen glycol | 79.9320 |
| oridonin* | 0.0180 |
| darutoside* | 0.0500 |

*Amount of pure darutoside and oridonin.

Formulation n° 5: Anti-Wrinkle Day Cream

| Starting materials | CTFA name | % | % |
|---|---|---|---|
| Phase A | | | |
| H₂O | | Qsp100 | Qsp100 |
| Ultrez 10 | Carbomer | 0.10 | 0.10 |

-continued

| Starting materials | CTFA name | % | % |
|---|---|---|---|
| Phase B | | | |
| Glycerin | Glycerin | 5.00 | 5.00 |
| Phase C | | | |
| Dermaxyl ™ | | — | 2.00 |
| Volpo S2 | Steareth 2 | 0.60 | 0.60 |
| Crodafos CES | Cetearyl alcohol dicetyl phosphate & Ceteth-10 phosphate | 4.00 | 4.00 |
| Crodamol STS | PPG-3 Benzyl Ether Myristate | 2.00 | 2.00 |
| Crodamol OSU | Dioctyl Succinate | 7.00 | 7.00 |
| Crill 3 | Sorbitan Stearate | 1.60 | 1.60 |
| Nipagine | Methyl Paraben | 0.30 | 0.30 |
| Phase D | | | |
| Potassium Sorbate | Potassium Sorbate | 0.10 | 0.10 |
| Phase E | | | |
| NaOH 30% | Sodium Hydroxide | 0.35 | 0.35 |
| H$_2$O | | 3.50 | 3.50 |
| Phase F | | | |
| P2 | | 3.00 | 3.00 |
| Phase G | | | |
| Fragrance | | 0.10 | 0.10 |

Operating Procedure:

Phase A: Sprinkle Ultrez 10 in the water, let swallow 20 minutes. Weigh phase B. Add phase B into phase A. Weigh phase C, heat phase A+phase B and phase C to 80° C. in a water bath. Under stirring staro v=30%, pour phase C into phase A+B, homogenize, then add phase D, homogenize. Then add at about 50° C. phase E. Add phase F around 35° C. Add phase G, mix well.

Formulation n° 6: Anti-Rednesses Lotion

| Starting materials | CTFA name | % |
|---|---|---|
| Phase A | | |
| H$_2$O | Water | Qsp100 |
| Phase B | | |
| Volpo G 26 | Glycereth 26 | 4.00 |
| Phenoxyethanol | Phenoxyethanol | 1.00 |
| Phase C | | |
| Crillet 1 | Polysorbate 20 | 2.00 |
| *Verbena* Fragrance | Fragrance | 0.10 |
| Phase D | | |
| P2 | | 3.00 |
| Phase E | | |
| Phytotonine ™ | | 5.00 |

Operating Procedure:

Weigh phase A. Weigh and mix phase B until complete solubilization. Then add phase B into phase A, stir under the propeller, v=300 rpm. Weigh and mix phase C. Add phase C into phase A+B, under propeller, v=300 rpm. Add phase D into phase A+B+C. Well homogenize, under propeller, v=300 rpm. Then add phase E in the previous phase. Well homogenize under propeller, v=300 rpm.

Formulation n° 7: Anti-Ageing Cream

| Starting materials | CTFA name | % |
|---|---|---|
| Phase A | | |
| H$_2$O | Water | Qsp100 |
| Ultrez 10 | Carbomer | 0.25 |
| Phase B | | |
| Butylene glycol | Butylene glycol | 2.00 |
| Phenoxyethanol | Phenoxytethanol | qs |
| Phase C | | |
| Volpo S 2 | Stereth-2 | 0.40 |
| Volpo S 10 | Stereth-10 | 1.20 |
| Crodafos CES | Cetearyl alcohol dicetyl phosphate & Ceteth-10 phosphate | 4.00 |
| Crodacol CS90 | Cetearyl Alcohol | 0.50 |
| Laurocapram | Azone | 2.50 |
| DC 345 | Cyclohexasiloxane (and) Cyclopentasiloxane | 2.00 |
| Crodamol OSU | Diethylhexyl Succinate | 7.00 |
| Phase D | | |
| Potassium sorbate | Potassium Sorbate | |
| Phase E | | |
| H$_2$O | Water | 3.00 |
| NaOH 30% | Sodium Hydroxide | 0.40 |
| Phase F | | |
| P2 | | 3.00 |
| Phase G | | |
| Oligoceane ™ | Maris Limus Extract and Ostrea Shell Extract and aqua and Propylene Glycol | 0.2 |
| Phase H | | |
| Venuceane ™ | Thermus Thermophillus Ferment and Glycerin | 2.00 |

Operating Procedure:

Weigh phase A and allow it to swell without stirring for 30 min Heat phase A at 75° C. in a water-bath. Weigh phase B and mix thoroughly. Add phase B into phase A at 75° C. in a water-bath. Weigh phase C and heat at 75° C. in a water-bath. Mix thoroughly. Pour phase C into phase A+B unde Staro stirring, rate: 1000 rpm. Mix thoroughly. Freshly add phase D. Add phase E, mix thoroughly. Adjust the pH to 6 with phase E at a temperature below 35° C. Add phase F, mix thoroughly. Add phase G, mix thoroughly. Then add phase H and mix thoroughly.

C—IN VIVO STUDIES

I In Vivo Test
Protocol
Study Inclusion Criteria:

Adult women of mean age 58 years having wrinkles and fine lines on the face or the neckline.

An initial joint panel of 12 subjects was used.

UV radiation and sun exposure sessions and tanning product applications were prohibited over the month preceding the study and during the study. The subjects were required to use only the cosmetics supplied throughout the duration of the study.

Study Type and Duration

The study was conducted using non-invasive methods, vs. a control site, each subject acting as its own control. The cream formulated with 3% of P1 (Formulation n° 1 without the ingredient Dermaxyl™) and the control cream were applied to opposite sides of the face; using massage, twice daily for 2 months, at the eye corner.

Safety

The products were well tolerated by all the subjects.
Studied parameter: Average depth of the main wrinkle

|  | Formulation n°1 | Placebo |
| --- | --- | --- |
| Diminution of the depth of the main wrinkle | Between −10 and −20% | −5% between +5% |

Significant difference between Formulation n° 1 and placebo is observed.

II In Vivo Studies with a Formulation Product Containing a Combination of Oridonin and Darutoside The Following Cream Products Were Used to Performe the Studies

| Starting materials | CTFA name | Cream composition according to the invention % | Placebo cream % |
| --- | --- | --- | --- |
| Phase A | | | |
| H₂O | Water | Qsp100 | Qsp100 |
| Ultrez 10 | Carbomer | 0.25 | 0.25 |
| Phase B | | | |
| Butylene glycol | Butylene glycol | 2.00 | 2.00 |
| Phenoxyethanol | Phenoxytethanol | qs | qs |
| Phase C | | | |
| Volpo S 2 | Stereth-2 | 0.40 | 0.40 |
| Volpo S 10 | Stereth-10 | 1.20 | 1.20 |
| Crodafos CES | Cetearyl alcohol dicetyl phosphate & Ceteth-10 phosphate | 4.00 | 4.00 |
| Crodacol CS90 | Cetearyl Alcohol | 0.50 | 0.50 |
| Laurocapram | Azone | 2.50 | 2.50 |
| DC 345 | Cyclohexasiloxane (and) Cyclopentasiloxane | 2.00 | 2.00 |
| Crodamol OSU | Diethylhexyl Succinate | 7.00 | 7.00 |
| Phase D | | | |
| Potassium sorbate | Potassium Sorbate | | |
| Phase E | | | |
| H₂O | Water | 3.00 | 3.00 |
| NaOH 30% | Sodium Hydroxide | 0.40 | 0.40 |
| Phase F | | | |
| Excipient | | 3.00 | — |
| P2 | | — | 3.00 |

Operating Procedure:

Weigh phase A and allow it to swell without stirring for 30 min. Heat phase A at 75° C. in a water-bath. Weigh phase B and mix thoroughly. Add phase B into phase A at 75° C. in a water-bath. Weigh phase C and heat at 75° C. in a water-bath. Mix thoroughly. Pour phase C into phase A+B unde Staro stirring, rate: 1000 rpm. Mix thoroughly. Freshly add phase D. Add phase E, mix thoroughly. Adjust the pH to 6 with phase E at a temperature below 35° C. Add phase F. Mix thoroughly.

Protocol of the Studies

Inclusion Criteria Specific to the Study

Adult women aged between 45 and 71 years (mean age: 58 years) with age spots (lengitines), hyperpigmented or red areas, fine lines and wrinkles on the face or neckline were selected. Subjects with two criteria in the same area were priority included.

An initial joint panel of 26 subjects was used. Each subject was subsequently classified as a function of chromophores. Since it was sometimes difficult to obtain, for all the subjects, the presence of the three pertinent chromophores at the same site, an optimal panel (meeting the screening criteria for each chromophore and site) of between 22 and 25 subjects was used.

Hormonal consistency over the 3 months preceding the study and during the study was required. UV radiation and sun exposure sessions and tanning product application were prohibited over the month preceding the study and during the study. The subjects were required to use only the cosmetics supplied throughout the duration of the study.

Study Type and Duration

The study was conducted using non-invasive methods, vs. a control site, each subject acting as its own control. The cream formulated with 3% of P2 (Foimulation n° 5) and the control cream were applied to opposite sides of the face and neckline, using massage, twice daily for 2 months.

Safety

The products were well tolerated by all the subjects.

1. Evaluation of the Chromophore Collagen by Echography and SIAscopy® a. Echography

The density of the dermis, and hence the density the collagen its principal component, can be determined by echography. Ultrasounds were emitted on the skin zone of interest using an echographic probe. The intensity of the sound waves reflected (or echoes) by the corresponding tissues is a function of tissue density. An analysis of the "slices" obtained enabled estimation of this variation in density.

Young skin is highly echogenic since it is denser than more elderly skin, which has areas of heterogeneity (variable numbers of irregular non-echogenic fields). The measurements given below, were recorded using a Dermascan C echograph system (Cortex) and a probe operating at a frequency of 20 MHz.

Using the SIAscope® system, it is possible to "see" to a depth of 2 mm under the skin.

Due to the problem of noise at the margins of the images, the peripheral crown was removed, in a standardized manner, using a SIAscan® analysis system developed for that purpose.

Each point (350,000 pixels/image) of the image has an intensity (gray scale) different from the point next to it. The sum of the intensities yields a mean and standard deviation which express the heterogeneity of collagen distribution over

TABLE 14

Change in dermal collagen density of the neckline (mean value; index; 25 subjects; n = 9 determinations)

| | Formulation n°5 | | | Control | | |
|---|---|---|---|---|---|---|
| | T0 | T 1 m | T 2 m | T0 | T 1 m | T 2 m |
| Mean | 14.58 +/− 2.6 | 15.97 +/− 3.6 | 17.13 +/− 3.9 | 13.98 +/− 2.6 | 14.21 +/− 2.3 | 15.57 +/− 3.8 |
| % change vs. T0 | | 9.6% | 17.5% | | 1.6% | 4.2% |
| significance | | p < 0.05 | p < 0.01 | | dns | dns |
| Significance vs. control | | p < 0.05 | p < 0.01 | | | |

With the cream according to the invention, there was a marked increase in the most echogenic zones reflecting an increase in the density of dermal fibers such as collagen. The increase, which was noteworthy and significant as of the first month of application, increased further after 2 months, reaching 17.5% (p<0.01). In parallel, the control site showed little change.

the image. This heterogeneity was monitored between two phases.

The results obtained were correlated with published results (MATTS et al., 2005) in order to express) the pre- vs. post-change in the heterogeneity of collagen distribution (equivalent to a standard deviation) as a variation in age.

TABLE 15

Change in the heterogeneity of collagen distribution over the face (mean standard deviation of collagen distribution; 25 subjects; n = 3 determinations)

| | Cream according to the invention | | | Control/placebo | | |
|---|---|---|---|---|---|---|
| | T0 | T 2 m | Difference in heterogeneity | T0 | T 2 m | Difference in heterogeneity |
| Mean standard deviation | 2.51 | 2.46 | −0.0515 | 2.475 | 2.475 | # 0 |
| Mean real age | 58 years | — | — | | | |
| Estimate of age change | — | 53.8 years | −4.2 years | | | # 0 |
| Significance vs. T0 | | p = 0.05 | | | dns | |
| Significance vs. control | | p < 0.05 | | | | | b. SIAscope®

The SIAscope® (Spectrophotometric Intracutaneous Analysis, AstronClinica) is a portable scanner combining the advantages of a camera and spectroscope.

On contact with the skin, the system takes a photograph and analyzes (from 400 to 1000 nm) the manner in which the light is absorbed or re-emitted by the skin.)

It is thus possible to quantify the various chromophores and, in particular, which renders the system unique for the time being, analyze the heterogeneity of the distribution of the chromophore, collagen.

2. Evaluation of the Red Chromophore Melanin, by VISIA®

The VISIA® System (Canfield) is a photographic chamber for the face that enables imaging under visible and cross-polarized light. Standardization of the images is ensured by a computer-aided repositioning system and by complete control of the photography conditions. From the pre-/post-images, it is possible to obtain:

the redness (or vascularization) index the melanin age spots index

These index are correlated with the number and intensity of age spots or rednesses in the skin area studied. For these two indexes, the VISIA® uses the RBXtm technology (Red/Brown subsurface analysis; Demerli et coll., 2007).

TABLE 16

Change in the vascularization index/redness of the face (mean value index; 24 subjects, n = 3 determinations)

| | Formulation n°5 | | | Control | | |
|---|---|---|---|---|---|---|
| | T0 | T 1 m | T 2 m | T0 | T 1 m | T 2 m |
| Mean | 1.206 +/− 0.380 | 1.107 +/− 0.322 | 1.076 +/− 0.438 | 1.218 +/− 1.093 | 1.113 +/− 0.393 | 1.085 +/− 0.411 |
| % change vs. T0 | | −8.2% | −10.8% | | 1.8% | −0.8% |
| Significance | | $p < 0.05$ | $p < 0.05$ | | dns | dns |
| Significance vs. control | | $p < 0.05$ | $p < 0.05$ | | | |

With the formulation n° 5, after the first month of application an important and significant improvement (p>0.05) of 8.2% of the vascularization index is observed.

The effect is improved after 2 months and reaches around 11% of improvement. Compared to the control, these improvements are very much better and significant ($p<0.05$).

3. Evaluation of the Brown Chromophore Haemoglobin; VISTA®

As explained before (paragraphe 2), the VISTA® analyses the melanin spot index.

In addition, through a database of manufacturer linking parameters of thousands of women to their age, it is possible to estimate the theoretical age of a skin (Lintner et al., 2007). This calculation is available, however, only to melanin spots.

TABLE 17

Change in the melanin chromophore melanin (melanin spots) on the face (mean value index; 24 subjects, n = 3 determinations).

| | Formulation n°5 | | | Control | | |
|---|---|---|---|---|---|---|
| | T0 | T 1 m | T 2 m | T0 | T 1 m | T 2 m |
| Mean | 3.93 +/− 1.34 | 3.76 +/− 1.18 | 3.63 +/− 1.19 | 3.80 +/− 1.30 | 3.83 +/− 1.34 | 3.71 +/− 1.17 |
| % change vs. T0 | | −4.3% | −7.6% | | 0.8% | −2.5% |
| Significance | | $p < 0.05$ | $p < 0.05$ | | dns | dns |
| Theoretical age gain vs. T0 | | −2.7 years | −4.8 years | | +0.5 years | −1.4 years |
| Significance vs. control | | $p < 0.05$ | $p < 0.05$ | | | |

After applying the formulation n° 5, from 1 month, a large and significant decrease of melanin spots is observed.

These decrease, in T 2 months, of almost 8%, which corresponds to a gain of approximately 5 years of age on this parameter.

Compared to the control that does not undergo little or no change, the effect is significant at T 1 month and T 2 months ($p<0.05$).

The invention claimed is:

1. A cosmetic composition comprising an effective amount of oridonin and darutoside and a physiological medium.

2. The composition according to claim 1 wherein the amount of oridonin ranges from 0.00001% to 50% by weight of the composition.

3. The composition according to claim 1 wherein the amount of darutoside ranges from 0.00001% to 80% by weight of the composition.

4. The composition according to claim 1 wherein the ratio of oridonin to darutoside ranges from 1:1000 to 10:1.

5. The composition according to claim 1 wherein the oridonin is extracted from *Rhabdosia rubescens*.

6. The composition according to claim 1 wherein the darutoside is extracted from *Siegesbeckia orientalis*.

7. A method of improving the general condition of skin comprising topically applying an effective amount of the composition of claim 1 to a subject in need thereof.

8. A method of treating signs of cutaneous aging comprising topically applying an effective amount of the composition of claim 1 to a subject in need thereof.

9. The method of claim 8 wherein said treating signs of cutaneous aging includes treating wrinkles, fine lines, visible and/or tactile skin discontinuities; loss of firmness, elasticity and tone of cutaneous tissue.

10. The method of claim 8 wherein said treating signs of cutaneous aging includes treating oxidative stress and free radicals.

11. The method of claim 8 wherein said treating signs of cutaneous aging includes treating deterioration of chromophore distribution by rebalancing the distribution of haemoglobin and collagen.

12. The method of claim 8 wherein said treating signs of cutaneous aging includes treating melanin spots.

13. The method of claim 8 wherein said treating signs of cutaneous aging includes reducing cutaneous redness.

14. The composition according to claim 1 wherein the amount of oridonin ranges from 0.0001% to 10% by weight of the composition.

15. The composition according to claim 1 wherein the amount of oridonin ranges from 0.001% to 3% by weight of the composition.

16. The composition according to claim 1 wherein the amount of darutoside ranges from 0.001% to 50% by weight of the composition.

17. The composition according to claim 1 wherein the amount of darutoside ranges from 0.01% to 3% by weight of the composition.

18. The composition according to claim 1 wherein the ratio of oridonin to darutoside ranges from 1:1000 to 1:1.

19. The composition according to claim 1 wherein the ratio of oridonin to darutoside ranges from 1:100 to 1.

20. The composition according to claim 1 further comprising at least one agent selected from the group consisting of *centella asiatica*, asiaticoside and asiatic acid, cafein, thein, theobromin, forskolin, esculin, esculoside, ACE inhibitors, Val-Trp, Neuropeptide Y inhibitors, enkephaline, *gingko biloba*, yam, *dioscorea* extract, rutin, yerba mate extract, guarana extract, oligosaccharides, exopolysaccharides, alcohol, carnitin, Ivy extract, focus extract, algae extract, *Peumus boldus* extract, palmitoylcarnitine, carnosine, taurine, cyclic AMP, and elderberry extract.

21. The composition according to claim 1 further comprising at least one additional active agent selected from the group consisting of anti-aging, whitening, moisturizing, slimming, revitalizing, anti-acne, anti-inflammatory and anti-hair loss agents.

22. The composition according to claim 21 wherein said anti-aging agent contains a *thermus* thermophiles ferment.

23. The composition according to claim 21 wherein said revitalizing agent contains mineral salts extracted from marine sediments and oyster shells.

24. The composition according to claim 1 further comprising one or more ingredients selected from the group consisting of cleaning agents, hair conditioning agents, skin conditioning agents, hair styling agents, antidandruff agents, hair growth promoters, perfumes, sunscreen compounds, sunblock compounds, pigments, moisturizers, film formers, hair colors, make-up agents, detergents, pharmaceuticals, thickening agents, emulsifiers, humectants, emollients, antiseptic agents, deodorant actives, surfactants and propellants.

25. The composition according to claim 1 wherein said composition is in the form of a solution, dispersion, emulsion, paste, or powder, individually or as a premix, or in vehicles individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, micro or nano emulsions, or adsorbed on organic polymer powders, talcs, bentonites, or other inorganic or organic supports.

26. The composition of claim 1 further comprising at least one compound capable of stimulating extracellular matrix.

27. The composition of claim 26 wherein said compound is selected from the group consisting of vitamin A, retinoic retinoid acid, retinol, retinoic acid, retinyl proprionate retinol palmitate, vitamin B3, niacinamide, nicotinate tocopherol, vitamin B5, vitamin B6, vitamin B12, vitamin C, ascorbic acid, ascorbyl acid, ascorbyl glucoside, ascorbyl tetrapalmitate, magnesium, sodium ascorbyl phosphate, vitamins E, F, H, K, PP, amino acids, arginine, ornithine, hydroxyproline, hydroxyproline dipalmitate, palmitoylglycine, peptides, copper peptides, Carnosine, allantoine, farnesol, biotine, adenosine, lactic acid, glycolic acid, glucosamine, acetylglucosamine, madecassic acid, asiaticoside and asiatic acids, ellagic acid, salicylic acid, stigmasterol, sitosterol, campesterol, brassicasterol, teprenone, genistein, equol, hexamidine, panthenol, dimethylaminoethanol (DMAE), oils containing DHA/EPA, shea butter, and glycerin.

28. The composition of claim 27 wherein the peptide is selected from the group consisting of the peptide of SEQ ID NO:1, SEQ ID NO: 2, SEQ ID NO:3, SEQ ID NO:4, and SEQ ID NO:5.

* * * * *